United States Patent
Chang et al.

(10) Patent No.: US 12,419,896 B2
(45) Date of Patent: *Sep. 23, 2025

(54) COMPOSITIONS AND DOSAGE FORMS FOR ORAL DELIVERY

(71) Applicant: RHODES TECHNOLOGIES, Coventry, RI (US)

(72) Inventors: Ping Chang, Waterford, CT (US); Marc Brown, Hertfordshire (GB); Charles Evans, West Sussex (GB)

(73) Assignee: RHODES TECHNOLOGIES, Coventry, RI (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/655,687

(22) Filed: May 6, 2024

(65) Prior Publication Data

US 2024/0358674 A1    Oct. 31, 2024

Related U.S. Application Data

(63) Continuation of application No. 17/054,272, filed as application No. PCT/US2019/031685 on May 10, 2019, now Pat. No. 12,011,430.

(60) Provisional application No. 62/670,374, filed on May 11, 2018.

(51) Int. Cl.
| | | |
|---|---|---|
| *A61K 31/352* | (2006.01) | |
| *A61K 9/00* | (2006.01) | |
| *A61K 31/05* | (2006.01) | |
| *A61K 47/06* | (2006.01) | |
| *A61K 47/10* | (2017.01) | |
| *A61K 47/44* | (2017.01) | |

(52) U.S. Cl.
CPC ............ *A61K 31/352* (2013.01); *A61K 9/006* (2013.01); *A61K 31/05* (2013.01); *A61K 47/06* (2013.01); *A61K 47/10* (2013.01); *A61K 47/44* (2013.01)

(58) Field of Classification Search
CPC ...... A61K 31/352; A61K 9/006; A61K 31/05; A61K 47/06; A61K 47/10; A61K 47/44; A61K 9/008; A61K 47/32; A61K 9/7015; A61K 9/7007; A61K 36/185; A61K 31/658; A61P 25/28; A61P 25/00; A61P 25/06

See application file for complete search history.

(56) References Cited

U.S. PATENT DOCUMENTS

| | | |
|---|---|---|
| 8,481,091 B2 | 7/2013 | Ross |
| 2003/0191180 A1 | 10/2003 | Ross |
| 2006/0160888 A1 | 7/2006 | Kottayil et al. |
| 2008/0112895 A1 | 5/2008 | Kottayil et al. |
| 2011/0306660 A1 | 12/2011 | Goskonda et al. |
| 2014/0242153 A1 | 8/2014 | Mannino et al. |
| 2016/0058866 A1 | 3/2016 | Sekura |
| 2018/0000731 A1 | 1/2018 | Eck et al. |

FOREIGN PATENT DOCUMENTS

| | | |
|---|---|---|
| CA | 2454644 | 2/2004 |
| KR | 10-2003-0074835 | 9/2003 |
| WO | 200264109 | 8/2002 |
| WO | 2016187156 | 11/2016 |

OTHER PUBLICATIONS

Babson, K. A.; Sottile, J.; Morabito, D. Cannabis, Cannabinoids, and Sleep: a Review of the Literature. Curr Psychiatry Rep, 19: 23, 1-12. (Year: 2017).*
International Search Report dated Jul. 25, 2019, issued in connection with international Application No. PCT/US2019/031685.
Written Opinion dated Jul. 25, 2019, issued in connection with international Application No. PCT/US2019/031685.
Extended European Search Report dated Mar. 1, 2022 in corresponding European Application No. 19799975.8.
Wikipedia, "1, 1, 1, 2-Tetrafluoroethane", https://en.wikipedia.org/wiki/1,1,1,2-Tetrafluoroethane, page last updated May 4, 2023, page retrieved Jun. 8, 2023.
Office Action issued Feb. 28, 2024 in connection with Canadian Patent Appln No. 3,099,980.
Office Action issued Apr. 11, 2024 in connection with Korean Patent Application No. 10-2020-7035388.

* cited by examiner

*Primary Examiner* — Jessica Worsham
(74) *Attorney, Agent, or Firm* — Troutman Pepper Locke LLP

(57) ABSTRACT

The present disclosure provides pharmaceutical compositions comprising a cannabinoid, and dosage forms comprising same, for oral delivery, such as sublingual or buccal delivery. The compositions of the present disclosure are substantially homogeneous and remain stable and monophasic upon storage. Also provided are methods of using the compositions for pain management and to treat various diseases and conditions, including dementia, sleep disorders, movement disorders, mental disorders, and multiple sclerosis.

19 Claims, 2 Drawing Sheets

COMPOSITIONS AND DOSAGE FORMS FOR ORAL DELIVERY

CROSS-REFERENCE TO RELATED APPLICATIONS

This application is a continuation of U.S. application Ser. No. 17/054,272, filed Nov. 10, 2020, which is a U.S. National Phase of International Patent Application No. PCT/US2019/031685, filed on May 10, 2019, which claims priority to U.S. Provisional Application No. 62/670,374, filed May 11, 2018, all of which are hereby incorporated herein by reference in their entireties.

FIELD OF INVENTION

The present disclosure relates to pharmaceutical compositions comprising a cannabinoid, and dosage forms comprising same, for oral delivery, such as sublingual or buccal delivery. The compositions of the present disclosure are homogeneous and remain stable upon storage. Also provided are methods of using the compositions for pain management and to treat various diseases and conditions such as dementia, sleep disorders, movement disorders, mental disorders and multiple sclerosis.

BACKGROUND OF THE INVENTION

Cannabinoids are a class of diverse chemical compounds that act on cannabinoid receptors in cells that alter neurotransmitter release in the brain. Ligands for these receptor proteins include the endocannabinoids, produced naturally in the body by animals, the phytocannabinoids, found in *Cannabis sativa* and some other plants, and synthetic cannabinoids, manufactured artificially. The most notable cannabinoid is the phytocannabinoid tetrahydrocannabinol (THC), the primary psychoactive compound in *Cannabis sativa*. Cannabidiol (CBD) is another major constituent of the plant.

An FDA-approved cannabinoid drug ingredient is (−)-trans-$\Delta^9$-tetrahydrocannabinol, also known as dronabinol, which is used as an appetite stimulant, an anti-emetic and an analgesic. At the present time, dronabinol and nabilone are the only commercially available FDA-approved cannabinoid drugs. Dronabinol has the following structural formula:

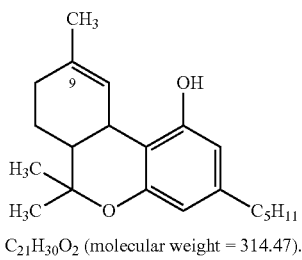

$C_{21}H_{30}O_2$ (molecular weight = 314.47).

Dronabinol is a clear to amber resinous oil that is sticky at room temperature and hardens upon refrigeration. Dronabinol is insoluble in water, but can be formulated in oil, e.g., sesame oil.

Dronabinol is commercially available as a solution in soft gelatin capsules for oral administration under the trade name Marinol®. Upon oral administration, the gelatin dissolves, releasing the drug. Dronabinol is then absorbed during its passage through the gastrointestinal tract. Marinol® is indicated for the treatment of: 1) anorexia associated with weight loss in patients with AIDS and 2) nausea and vomiting associated with cancer chemotherapy in patients who have failed to respond adequately to conventional antiemetic treatments. Dronabinol is formulated with the following inactive ingredients: sesame oil, gelatin, glycerin, (glycerol), methylparaben, propylparaben, and titanium dioxidein Marinol® capsules, which are sold in 2.5 mg. 5 mg, or 10 mg dosages.

Dronabinol in the Marinol® soft gelatin capsule formulation is highly unstable at room temperature, and it is recommended that the product be stored at refrigerated (2-8° C.) or cool (8-15° C.) conditions (Marinol® package label, Physicians Desk Reference®, ed. 2003). Additionally, Marinol® should be packaged in a dark, well-closed container and stored in a cool environment between 8° C. and 15° C. (46° F. and 59° F.). Additionally, due to absorption through the GI tract, Marinol® affords low bioavailability of dronabinol. Marinol® also suffers from variable pharmacokinetics due to first pass metabolism, and is difficult to take by patients suffering from emesis and anorexia.

At the present time, dronabinol and nabilone are the only commercially available approved cannabinoid drugs in the United States. In Europe and Canada, Sativex®, a sublingual spray containing dronabinol and cannabidiol in a ratio of 52:48, is also available for the treatment of multiple sclerosis spasticity. Sativex®, manufactured by GW Pharmaceuticals, is described in U.S. Pat. No. 8,512,767, Like Marinol®, Sativex® must also be refrigerated to maintain chemical stability. Similar to Marinol®, limitations of Sativex® include poor storage stability and pharmacokinetics.

Drug delivery via the oral mucous membrane is considered to be a promising alternative to the oral route. Oral spray formulations for sublingual or buccal administration offer multiple advantages over solid oral dosage forms, such as enabling the drug to be absorbed directly through the mucosal lining beneath the tongue which has a very rich vascular blood supply, resulting in faster onset. Parmar, K. et al, 2017:8 (11): 4533-4539. Further, an oral spray formulation avoids the issues associated with first pass metabolism. As such, a sublingual spray may be advantageous when rapid onset of action and better efficacy is desired. An oral spray may result in better compliance than orally ingested forms, such as tablets or capsules, by patients who have difficulty swallowing or suffering from emesis and anorexia.

Composition stability and dosage uniformity remain technical challenges when formulating sublingual sprays in general. These challenges become even greater when the active ingredient presents stability and solubility challenges, as is the case with cannabinoids. Particularly challenging is the manufacture of a homogeneous cannabinoid oral spray formulation that remains monophasic and does not separate upon storage.

Thus, there exists an unmet need for improved compositions comprising a cannabinoid for oral delivery via the sublingual or buccal route that are stable, well-tolerated, and have enhanced activity. The compositions and methods described herein are directed towards these and other goals.

SUMMARY OF THE INVENTION

Various non-limiting aspects and embodiments of the disclosure are described below:

In one aspect, the present disclosure provides pharmaceutical compositions comprising a cannabinoid, or a derivative thereof, a hydrophobic solvent, an alcohol-based solvent, an optional co-solvent, a film-forming agent, and about 49% w/w to about 61% w/w of a propellant, wherein the pharmaceutical composition is an oral liquid pharmaceutical composition, and wherein the pharmaceutical composition is substantially anhydrous. Specifically, the pharmaceutical compositions of the disclosure comprising about 49% w/w to about 61% w/w of a propellant result in homogeneous compositions. In one embodiment, the pharmaceutical composition of the disclosure is a single active pharmaceutical ingredient composition comprising a cannabinoid as the single pharmaceutical ingredient.

In some embodiments, the pharmaceutical compositions of the disclosure are homogeneous. In one embodiment, the pharmaceutical compositions of the disclosure remain stable upon storage for at least two years at about 4° C., or at least one month at room temperature (e.g., about 23° C.).

The pharmaceutical compositions of the disclosure comprise a cannabinoid, or a pharmaceutically acceptable salt, solvate or derivative thereof. In one embodiment, the cannabinoid is selected from (−)-trans-$\Delta^9$-tetrahydrocannabinol (dronabinol), cannabidiol (CBD), pharmaceutically acceptable salts, solvate or derivatives thereof and combinations thereof. In one embodiment, the cannabinoid is (−)-trans-$\Delta^9$-tetrahydrocannabinol (dronabinol), or a pharmaceutically acceptable salt thereof. In one embodiment, the pharmaceutical compositions of the disclosure comprise from about 0.025% w/w to about 40% w/w of a cannabinoid. In one embodiment, the pharmaceutical compositions of the disclosure comprise from about 0.25% w/w to about 10% w/w of a cannabinoid. In one embodiment, the pharmaceutical compositions of the disclosure comprise from about 0.25% w/w to about 2% w/w of a cannabinoid.

In one embodiment, the pharmaceutical compositions comprise about 2% w/w to about 10% w/w of a hydrophobic solvent. In one embodiment, the pharmaceutical compositions comprise a hydrophobic solvent which is an oil-based solvent. In one embodiment, the hydrophobic solvent is an oil-based solvent selected from sesame oil, soybean oil, hydrogenated vegetable oil, and combinations thereof. In one embodiment, the oil-based solvent is sesame oil.

In another embodiment, the pharmaceutical compositions comprise a hydrophobic solvent which is an alkane solvent, e.g., a $C_5$-$C_{12}$ alkane solvent. In one embodiment, the hydrophobic solvent is a $C_5$-$C_{12}$ alkane solvent selected from pentane, hexane, heptane, and combinations thereof.

In one embodiment, the pharmaceutical compositions comprise about 30% w/w to about 60% w/w of an alcohol-based solvent. In one embodiment, the pharmaceutical compositions comprise an alcohol-based solvent selected from ethanol, isopropanol, n-propanol and combinations thereof. In one embodiment, the alcohol-based solvent is isopropanol.

In one embodiment, the pharmaceutical compositions comprise a co-solvent. In one embodiment, the pharmaceutical compositions comprise about 0.5% w/w to about 5% w/w of a co-solvent. In one embodiment, the co-solvent is selected from benzyl alcohol, propylene glycol, dipropylene glycol, glycerol, dimethicone 350, dimethicone 1000 and combinations thereof. In one embodiment, the co-solvent is an additional alcohol-based solvent. In one embodiment, the co-solvent is benzyl alcohol. In one embodiment, the co-solvent is propylene glycol.

In one embodiment, the pharmaceutical compositions comprise about 0.1% w/w to about 1% w/w of a film forming agent. In one embodiment, the film forming agent is a polymer selected from polyvinyl pyrolidone, polyvinyl alcohol, acrylic polymers, acrylic copolymers, methacrylate polymers, methacrylate copolymers, polyvinyl acetate, cellulose based polymers, and cellulose based copolymers.

In one embodiment, the pharmaceutical compositions of the disclosure comprise from about 49% w/w to about 61% w/w of a propellant. In one embodiment, the pharmaceutical compositions of the disclosure comprise from about 49% w/w to about 54% w/w of a propellant. In one embodiment, the propellant is hydrofluoroalkane selected from 1,1,1,2-tetrafluoroethane (HFC-134a) and 1,1,1,2,3,3,3-Heptafluoropropane (HFC-227), or a chlorofluorocarbon (CFC) selected from CFC 11, CFC 12, and CFC 114, and combinations thereof.

In one embodiment, the pharmaceutical composition according to the disclosure comprises:
a. about 0.25% w/w to about 2% w/w of dronabinol, or a pharmaceutically acceptable salt thereof;
b. about 2% w/w to about 10% w/w of a hydrophobic solvent (e.g., sesame oil);
c. about 30% w/w to about 60% w/w of an alcohol-based solvent (e.g., isopropyl alcohol);
d. about 0.5% w/w to about 5% w/w of a co-solvent (e.g., selected from benzyl alcohol and propylene glycol);
e. about 0.1% w/w to about 1% w/w of a film-forming agent (e.g., Eudragit E100),
f. and about 49% w/w to about 61% w/w of a propellant (e.g., 1,1,1,2-tetrafluoroethane).

In one embodiment, the pharmaceutical compositions of the disclosure further comprise a flavorant to impart a pleasant flavor to the formulation, which may aide in palatability. In some embodiments, the flavorant may be selected from, but are not limited to, menthol, levomenthol, peppermint flavoring, and cinnamon flavoring in a solvent, such as an alcohol-based solvent or an oil-based solvent.

In another aspect, the present disclosure provides a spray for oral application comprising an oral liquid composition comprising about 0.025% w/w to about 40% w/w of a cannabinoid, or a derivative thereof, a hydrophobic solvent, an alcohol-based solvent, an optional co-solvent, a film former, and about 49% w/w to about 61% w/w of a propellant, wherein the composition is substantially anhydrous. In one embodiment, the spray is for buccal application. In one embodiment, the spray is for sublingual application.

In one embodiment, the sprays of the disclosure comprise compositions that are homogeneous. In one embodiment, the sprays of the disclosure remain stable upon storage for at least two years at refrigerated temperature (e.g., about 2-8° C., or about 4° C.), or at least one month at room temperature (e.g., about 23° C.).

In one embodiment, the cannabinoid is (−)-trans-$\Delta^9$-tetrahydrocannabinol (dronabinol), or a pharmaceutically acceptable salt thereof. In one embodiment, the spray comprises from about 0.025% w/w to about 40% w/w of a cannabinoid. In one embodiment, the spray comprises from about 0.25% w/w to about 10% w/w of a cannabinoid. In one embodiment, the spray comprises from about 0.25% w/w to about 2% w/w of a cannabinoid.

In one embodiment, the spray comprises a hydrophobic solvent which is an oil-based solvent. In one embodiment, the hydrophobic solvent is an oil-based solvent selected from sesame oil, soybean oil, hydrogenated vegetable oil, and combinations thereof. In one embodiment, the oil-based solvent is sesame oil.

In another embodiment, the spray comprises a hydrophobic solvent which is an alkane solvent, e.g., a $C_5$-$C_{12}$ alkane solvent. In one embodiment, the hydrophobic solvent is a $C_5$-$C_{12}$ alkane solvent selected from pentane, hexane, heptane, and combinations thereof.

In one embodiment, the spray according to the disclosure comprises:
a. about 0.25% w/w to about 2% w/w of dronabinol, or a pharmaceutically acceptable salt thereof;
b. about 2% w/w to about 10% w/w of a hydrophobic solvent (e.g., sesame oil);
c. about 30% w/w to about 60% w/w of an alcohol-based solvent (e.g., isopropyl alcohol);
d. about 0.5% w/w to about 5% w/w of a co-solvent (e.g., selected from benzyl alcohol and propylene glycol);
e. about 0.1% w/w to about 1% w/w of a film-forming agent (e.g., Eudragit E100),
f. and about 49% w/w to about 61% w/w of a propellant (e.g., 1,1,1,2-tetrafluoroethane).

In one embodiment, the spray according to the disclosure is a multi-dose spray delivering between 20 and 200 microliters of the composition per dose. In one embodiment, the spray is contained in a metal canister. In one embodiment, the metal canister comprises between about 10 ml and about 100 ml of the composition.

In one aspect, the present disclosure provides pharmaceutical compositions comprising a cannabinoid, or a pharmaceutically acceptable salt, solvate or derivative thereof, a hydrophobic solvent, an alcohol-based solvent, an optional co-solvent, and about 49% w/w to about 61% w/w of a propellant, wherein the pharmaceutical composition is an oral liquid pharmaceutical composition, and wherein the pharmaceutical composition is free from film-forming agents and substantially anhydrous.

In one embodiment, the pharmaceutical compositions of the disclosure are homogeneous. In one embodiment, the pharmaceutical compositions of the disclosure remain stable upon storage for at least two years at about 4° C., or at least one month at room temperature (e.g., about 23° C.).

In one embodiment, the cannabinoid is selected from (−)-trans-$\Delta^9$-tetrahydrocannabinol (dronabinol), cannabidiol (CBD), or pharmaceutically acceptable salts or derivatives thereof and combinations thereof. In one embodiment, the cannabinoid is (−)-trans-$\Delta^9$-tetrahydrocannabinol (dronabinol), or a pharmaceutically acceptable salt thereof. In one embodiment, the pharmaceutical compositions of the disclosure comprise from about 0.025% w/w to about 40% w/w of a cannabinoid. In one embodiment, the pharmaceutical compositions of the disclosure comprise from about 0.25% w/w to about 10% w/w of a cannabinoid. In one embodiment, the pharmaceutical compositions of the disclosure comprise from about 0.25% w/w to about 2% w/w of a cannabinoid.

In one embodiment, the pharmaceutical compositions comprise about 2% w/w to about 10% w/w of a hydrophobic solvent. In one embodiment, the pharmaceutical compositions comprise a hydrophobic solvent which is an oil-based solvent. In one embodiment, the hydrophobic solvent is an oil-based solvent selected from sesame oil, soy bean oil, hydrogenated vegetable oil, and combinations thereof. In one embodiment, the oil-based solvent is sesame oil.

In another embodiment, the pharmaceutical compositions comprise a hydrophobic solvent which is an alkane solvent, e.g., a $C_5$-$C_{12}$ alkane solvent. In one embodiment, the hydrophobic solvent is a $C_5$-$C_{12}$ alkane solvent selected from pentane, hexane, heptane, and combinations thereof.

In one embodiment, the pharmaceutical compositions comprise about 30% w/w to about 60% w/w of an alcohol-based solvent. In one embodiment, the pharmaceutical compositions comprise an alcohol-based solvent selected from ethanol, isopropanol, n-propanol and combinations thereof. In one embodiment, the alcohol-based solvent is isopropanol.

In one embodiment, the pharmaceutical compositions comprise a co-solvent. In one embodiment, the pharmaceutical compositions comprise about 0.5% w/w to about 5% w/w of a co-solvent. In one embodiment, the co-solvent is selected from benzyl alcohol, propylene glycol, dipropylene glycol, glycerol, dimethicone 350, dimethicone 1000 and combinations thereof. In one embodiment, the co-solvent is an additional alcohol-based solvent. In one embodiment, the co-solvent is benzyl alcohol. In one embodiment, the co-solvent is propylene glycol.

In one embodiment, the pharmaceutical compositions of the disclosure comprise from about 49% w/w to about 61% w/w of a propellant. In one embodiment, the pharmaceutical compositions of the disclosure comprise from about 49% w/w to about 54% w/w of a propellant. In one embodiment, the propellant is hydrofluoroalkane selected from 1,1,1,2-tetrafluoroethane (HFC-134a) and 1,1,1,2,3,3,3-Heptafluoropropane (HFC-227), or a chlorofluorocarbon selected from CFC 11, CFC 12, and CFC 114, and combinations thereof.

In one embodiment, the pharmaceutical composition according to the disclosure comprises:
a. about 0.25% w/w to about 10% w/w of dronabinol, or a pharmaceutically acceptable salt thereof;
b. about 2% w/w to about 10% w/w of a hydrophobic solvent (e.g., sesame oil);
c. about 30% w/w to about 60% w/w of an alcohol-based solvent (e.g., isopropyl alcohol);
d. about 0.5% w/w to about 5% w/w of a co-solvent (e.g., propylene glycol),
e. and about 49% w/w to about 61% w/w of a propellant (e.g., 1,1,1,2-tetrafluoroethane).

In one embodiment, the pharmaceutical compositions of the disclosure further comprise a flavorant.

In another aspect, the present disclosure provides a spray for oral application comprising an oral liquid composition comprising a cannabinoid, or a derivative thereof, a hydrophobic solvent, an alcohol-based solvent, an optional co-solvent, and about 49% w/w to about 61% w/w of a propellant, wherein the composition is free from film-forming agents and substantially anhydrous. In one embodiment, the spray is for buccal application. In one embodiment, the spray is for sublingual application.

In one embodiments, the sprays of the disclosure comprise compositions that are homogeneous. In one embodiments, the sprays of the disclosure remain stable upon storage for at least two years at about 4° C., or at least one month at about 23° C.

In one embodiment, the cannabinoid is (−)-trans-$\Delta^9$-tetrahydrocannabinol (dronabinol), or a pharmaceutically acceptable salt thereof. In one embodiment, the spray comprises from about 0.025% w/w to about 40% w/w of a cannabinoid. In one embodiment, the spray comprises from about 0.25% w/w to about 10% w/w of a cannabinoid. In one embodiment, the spray comprises from about 0.25% w/w to about 2% w/w of a cannabinoid.

In one embodiment, the spray comprises a hydrophobic solvent which is an oil-based solvent. In one embodiment, the hydrophobic solvent is an oil-based solvent selected from sesame oil, soybean oil, hydrogenated vegetable oil, and combinations thereof. In one embodiment, the oil-based solvent is sesame oil.

In another embodiment, the spray comprises a hydrophobic solvent which is an alkane solvent, e.g., a $C_5$-$C_{12}$ alkane solvent. In one embodiment, the hydrophobic solvent is a $C_5$-$C_{12}$ alkane solvent selected from pentane, hexane, heptane, and combinations thereof.

In one embodiment, the spray according to the disclosure is substantially anhydrous and comprises an oral liquid composition comprising:
a. about 0.25% w/w to about 10% w/w of dronabinol, or a pharmaceutically acceptable salt thereof;
b. about 2% w/w to about 10% w/w of a hydrophobic solvent (e.g., sesame oil);
c. about 30% w/w to about 60% w/w of an alcohol-based solvent (e.g., isopropyl alcohol);
d. about 0.5% w/w to about 5% w/w of a co-solvent (e.g., propylene glycol),
e. and about 49% w/w to about 61% w/w w/w of a propellant (e.g., 1,1,1,2-tetrafluoroethane).

In one embodiment, the spray according to the disclosure is substantially anhydrous and comprises an oral liquid composition comprising:
a. about 2% w/w of dronabinol, or a pharmaceutically acceptable salt thereof;
b. about 2.2% w/w of a hydrophobic solvent (e.g., sesame oil);
c. about 40% w/w of an alcohol-based solvent (e.g., isopropyl alcohol);
d. about 2.0% w/w of a co-solvent (e.g., propylene glycol),
e. and about 53.8% w/w of a propellant (e.g., 1,1,1,2-tetrafluoroethane).

In one embodiment, the spray according to the disclosure is a multi-dose spray device delivering between 20 and 200 microliters of the composition per dose. In one embodiment, the spray is contained in a metal canister. In one embodiment, the metal canister comprises between about 10 ml and about 100 ml of the composition.

In some embodiments, the compositions and dosage forms of the disclosure are useful for treating, ameliorating, or alleviating the symptoms of pain (e.g., migraine, neuropathic pain, trigeminal pain), dementia (e.g., Alzheimer's disease, mild cognitive impairment), a sleep disorder (e.g., sleep apnea, narcolepsy), a movement disorder (e.g., Tourette's syndrome, Parkinson's disease), a mental disorder (e.g., posttraumatic stress disorder), and multiple sclerosis (e.g., pain associated with multiple sclerosis, incontinence associated with multiple sclerosis).

In some particular embodiments, the compositions and dosage forms of the disclosure are useful for treating migraine. In some particular embodiments, the pharmaceutical compositions of the disclosure are useful for treating, ameliorating, or alleviating symptoms of Alzheimer's disease. In certain embodiments, the pharmaceutical compositions of the disclosure are useful for treating or preventing Alzheimer's disease.

In some particular embodiments, the compositions and dosage forms of the present disclosure can be used for the treatment for symptomatic relief of spasticity (muscle stiffness/spasm) and/or neuropathic pain due to multiple sclerosis (MS). In certain embodiments, the compositions and dosage forms of the present disclosure can be used for the analgesic treatment for cancer patients. In a particular embodiment, the cancer patients are those who experience pain while on opioid therapy.

In some particular embodiments, the compositions and dosage forms of the disclosure can be used to treat chemotherapy-induced emesis, nausea, and/or vomiting in patients with cancer, to treat HIV/AIDS-related anorexia, and/or as an appetite stimulant.

In another aspect, the present disclosure provides a method of treating, ameliorating, or alleviating the symptoms of a disease, disorder or condition in a subject in need of such treatment, the method comprising administering to the subject a therapeutically effective amount of the pharmaceutical composition or dosage form of the disclosure. The disease, disorder or condition includes pain (e.g., migraine, neuropathic pain, trigeminal pain), dementia (e.g., Alzheimer's disease, mild cognitive impairment), a sleep disorder (e.g., sleep apnea, narcolepsy), a movement disorder (e.g., Tourette's syndrome, Parkinson's disease), a mental disorder (e.g., posttraumatic stress disorder), and multiple sclerosis (e.g., pain associated with multiple sclerosis, incontinence associated with multiple sclerosis).

In one embodiment, the present disclosure provides a method of treating migraine in a subject in need of such treatment, the method comprising administering to the subject a therapeutically effective amount of the pharmaceutical composition or dosage form of the disclosure.

In one embodiment, the present disclosure provides a method of treating, ameliorating, or alleviating the symptoms of Alzheimer's disease in a subject in need of such treatment, the method comprising administering to the subject a therapeutically effective amount of the pharmaceutical composition or dosage form of the disclosure. A method of treating or preventing Alzheimer's disease is also provided.

In some embodiments, the compositions and dosage forms are administered at least once a day. In other embodiments, the administering occurs more than once a day, e.g., 2 times, 3 times, 4 times, 5 times, 6 times, 7 times, 8 times, 9 times, or 10 times a day. In one embodiment, the administering is once a day. In one embodiment, the administering is 2 times a day.

In some embodiments, the compositions and dosage forms of the disclosure are administered orally.

These and other aspects of the present disclosure will become apparent to those skilled in the art after a reading of the following detailed description of the disclosure, including the appended claims.

DETAILED DESCRIPTION

Figure 1:
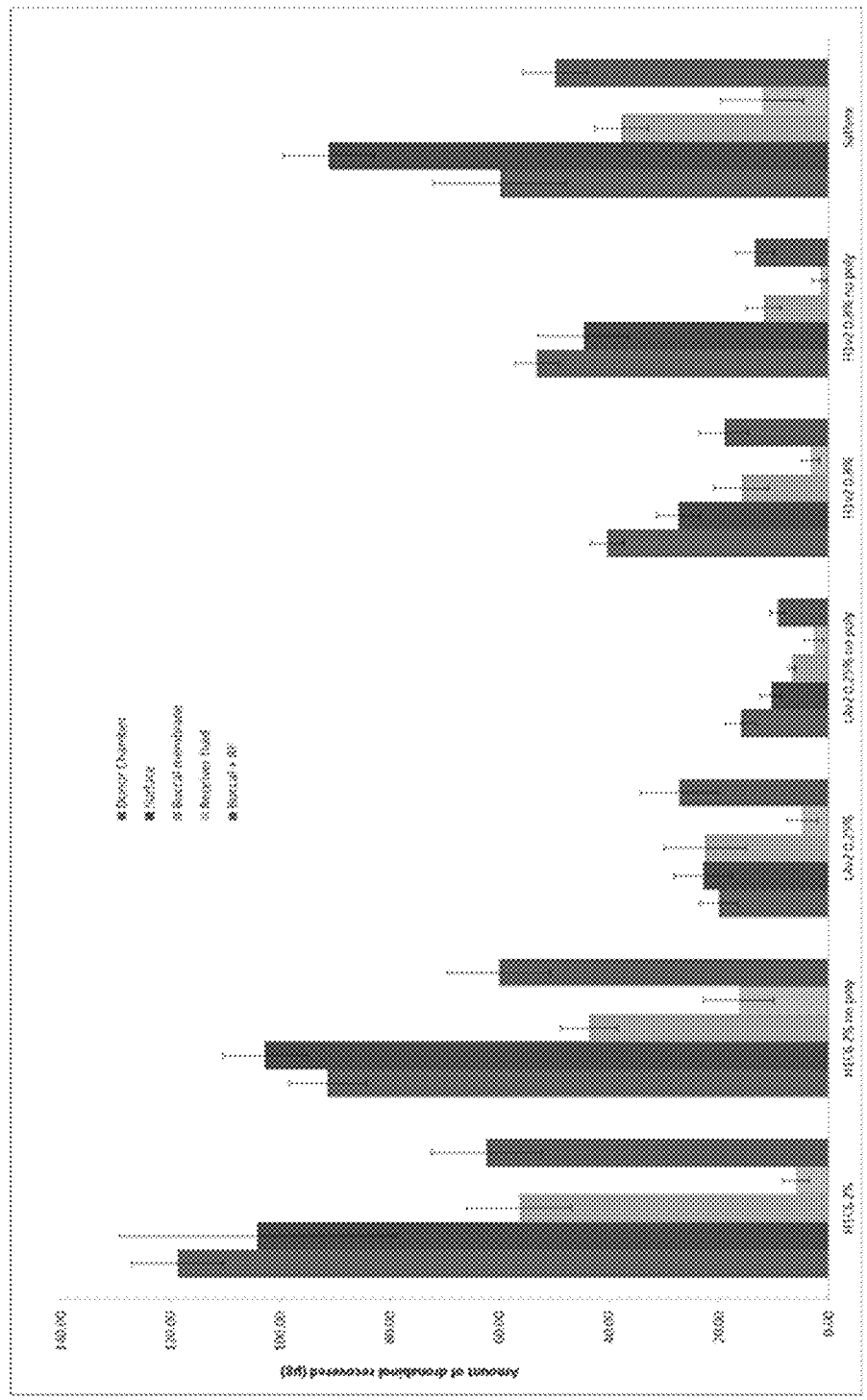
FIG. 1 depicts the mean amount of dronabinol recovered (µg) following the final time point (t=24 h) from the donor chamber, surface, buccal membrane, receiver fluid (RF) and buccal+RF (combination of buccal membrane and receiver fluid).

Detailed embodiments of the present invention are disclosed herein: however, it is to be understood that the disclosed embodiments are merely illustrative of the invention that may be embodied in various forms. In addition, each of the examples given in connection with the various embodiments of the invention is intended to be illustrative, and not restrictive. Therefore, specific structural and functional details disclosed herein are not to be interpreted as limiting, but merely as a representative basis for teaching one skilled in the art to variously employ the present invention.

DEFINITIONS

Unless defined otherwise, all technical and scientific terms used herein have the same meaning as commonly understood by one of ordinary skill in the art to which this invention belongs.

As used in this specification and the appended claims, the singular forms "a", "an", and "the" include plural references unless the context clearly dictates otherwise. Thus, for example, a reference to "a method" includes one or more methods, and/or steps of the type described herein and/or which will become apparent to those persons skilled in the art upon reading this disclosure.

The terms "treat" or "treatment" of a state, disorder or condition include: (1) preventing, delaying, or reducing the incidence and/or likelihood of the appearance of at least one clinical or sub-clinical symptom of the state, disorder or condition developing in a subject that may be afflicted with or predisposed to the state, disorder or condition but does not yet experience or display clinical or subclinical symptoms of the state, disorder or condition: or (2) inhibiting the state, disorder or condition, i.e., arresting, reducing or delaying the development of the disease or a relapse thereof or at least one clinical or sub-clinical symptom thereof: or (3) relieving the disease, i.e., causing regression of the state, disorder or condition or at least one of its clinical or sub-clinical symptoms. The benefit to a subject to be treated is either statistically significant or at least perceptible to the patient or to the physician.

A "subject" or "patient" or "individual" or "animal", as used herein, refers to humans, veterinary animals (e.g., cats, dogs, cows, horses, sheep, pigs, etc.) and experimental animal models of diseases (e.g., mice, rats). In one embodiment, the subject is a human.

As used herein the term "effective" applied to dose or amount refers to that quantity of a compound or pharmaceutical composition that is sufficient to result in a desired activity upon administration to a subject in need thereof. Note that when a combination of active ingredients is administered, the effective amount of the combination may or may not include amounts of each ingredient that would have been effective if administered individually. The exact amount required will vary from subject to subject, depending on the species, age, and general condition of the subject, the severity of the condition being treated, the particular drug or drugs employed, the mode of administration, and the like.

The phrase "pharmaceutically acceptable", as used in connection with compositions of the disclosure, refers to molecular entities and other ingredients of such compositions that are physiologically tolerable and do not typically produce untoward reactions when administered to a mammal (e.g., a human). Preferably, as used herein, the term "pharmaceutically acceptable" means approved by a regulatory agency of the Federal or a state government or listed in the U.S. Pharmacopeia or other generally recognized pharmacopeia for use in mammals, and more particularly in humans.

The phrase "therapeutically effective amount," as used herein, refers to an amount that produces the desired effect for which it is administered. The exact amount will depend on the purpose of the treatment and will be ascertainable by one skilled in the art using known techniques (see, for example, Lloyd (1999) The Art, Science and Technology of Pharmaceutical Compounding).

Ranges can be expressed herein as from "about" or "approximately" one particular value and/or to "about" or "approximately" another particular value. When such a range is expressed, another embodiment includes from the one particular value and/or to the other particular value.

By "comprising" or "containing" or "including" is meant that at least the named compound, element, particle, or method step is present in the composition or article or method, but does not exclude the presence of other compounds, materials, particles, or method steps, even if the other such compounds, material, particles, or method steps have the same function as what is named.

As described in detail below, the present inventors have discovered, after extensive investigation, that specific combinations of solvents, co-solvents, and a propellant produce oral liquid pharmaceutical compositions comprising a cannabinoid that are homogeneous and stable upon storage. Surprisingly, the pharmaceutical compositions of the disclosure comprising about 49% w/w to about 61% w/w of a propellant result in homogeneous compositions that remain stable upon storage for at least two years at about 4° C., or at least one month at about 23° C. As used herein, "stable" compositions are both physically and chemically stable, i.e., they remain homogenous without phase separation, without substantial purity changes, and/or without significant impurity profile changes.

Unless defined otherwise, all technical and scientific terms used herein have the same meaning as commonly understood by one of ordinary skill in the art to which this invention belongs.

Cannabinoid

The term "cannabinoid" or "cannabinoid derivative" relates to any cannabinoid isolated from the *Cannabis sativa* plant or synthetically created compound that interacts with a cannabinoid receptor or is a cannabinoid mimetic and/or derivative, including tetrahydrocannabinol (THC), cannabidiol (CBD), cannabinol (CBN), and dodeca-E,4E,8Z,10E/Z-tetraenoic-acid-isobutylamides, cannabigerol (CBG), cannabichromene, cannabicyclol (CBL), cannabivarin (CBV), tetrahydrocannabivarin (THCV), cannabidivarin (CBDV), cannabichromevarin (CBCV), cannabigerovarin (CBGV), and cannabigerol monomethylether (CBGM).

In some embodiments, the active pharmaceutical ingredient in the composition is tetrahydrocannabinol (THC) or a pharmaceutically acceptable salt thereof. THC exists in many isomeric forms, including (+)-trans-$\Delta^8$-tetrahydrocannabinol, (−)-trans-$\Delta^8$-tetrahydrocannabinol, (+)-trans-$\Delta^9$-tetrahydrocannabinol, and (−)-trans-$\Delta^9$-tetrahydrocannabinol (or dronabinol; trade name Marinol®). Structures of THC positional and stereoisomers is shown in Scheme 1.

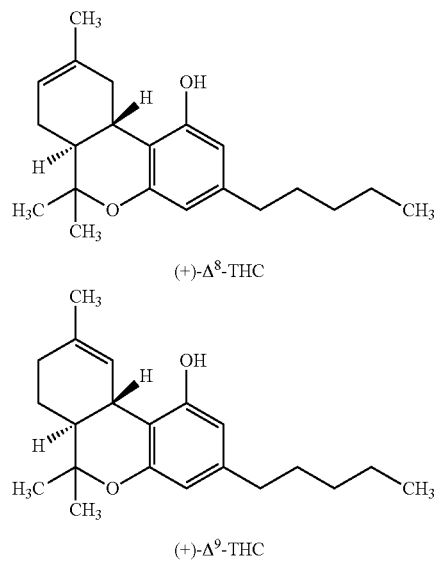

Scheme 1

(+)-$\Delta^8$-THC (+)-$\Delta^9$-THC

-continued

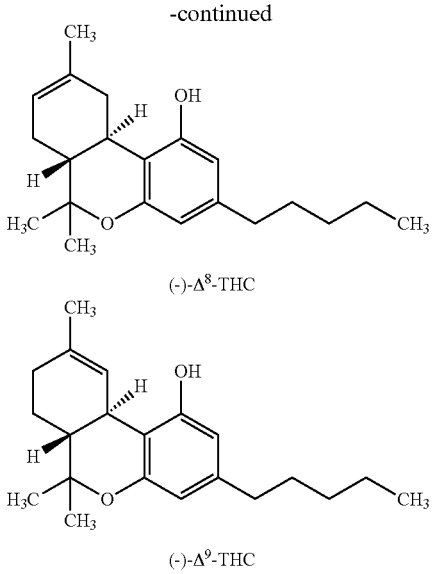

(−)-trans-Δ⁹-THC (dronabinol) is the major natural constituent of *Cannabis sativa*. Δ⁹-THC and Δ⁸-THC have essentially identical pharmacological profiles and their solubilities are essentially identical. Although Δ⁸-THC is more stable, does not undergo oxidation to cannabinol and has a much longer shelf life than Δ⁹-THC, it is less potent in most pharmacological tests (see, e.g., Ophthalmic Res. (1992) 24:142-149). Thus, there is a need for stabilized formulations comprising Δ⁹-THC (dronabinol) and other active cannabinoid compounds and derivatives.

In some embodiments, the cannabinoid employed in the present disclosure is (−)-trans-Δ⁹-tetrahydrocannabinol (dronabinol), or a pharmaceutically acceptable salt thereof.

In some embodiments, the cannabinoid employed in the present disclosure is (−)-trans-Δ⁸-tetrahydrocannabinol, or a pharmaceutically acceptable salt thereof.

The cannabinoid may be present in the compositions of the present disclosure at about 0.025% w/w to about 10% w/w cannabinoid, or at about 0.025% w/w to about 5% w/w cannabinoid, or at about 0.05% to about 5%, or at about 0.1% to about 5%, or at about 0.25% w/w to about 2.5% w/w cannabinoid, or about 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5% w/w cannabinoid.

In some embodiments, the composition comprises about 0.8% w/w cannabinoid.

In some embodiments, the composition comprises about 2.0% w/w cannabinoid.

In some embodiments, a cannabinoid (e.g., (−)-trans-Δ⁹-tetrahydrocannabinol (dronabinol), or a pharmaceutically acceptable salt or solvate thereof) is the only cannabinoid compound present in the composition. In some embodiments, the composition is substantially free of other cannabinoid compounds and/or cannabinoid degradation products.

In some embodiments, the composition is substantially free of certain cannabinoid compounds, e.g., CBD and/or CBG.

In some embodiments, the emulsion composition is substantially free of Δ⁸-THC.

In some embodiments, the cannabinoid is combined with other active pharmaceutical ingredients in the composition. The other active pharmaceutical ingredients include, for example, active pharmaceutical ingredients generally considered as suitable for sublingual or buccal use (e.g., fentanyl and nitroglycerin).

Propellant

The compositions of the disclosure comprise at least one propellant as the delivery vehicle. As used herein, the term "propellant" refers to any volatile short chain hydrocarbon, hydrofluoroalkane, or chlorofluorocarbon approved by the Food and Drug Administration for use in pressurized containers to create movement of a fluid from the dispenser.

In some embodiments, the propellant may be a hydrofluoroalkane (HFA). HFA propellants are volatile, non-toxic, non-flammable, and environmentally friendly, which makes them an excellent delivery vehicle for spray formulations. In some embodiments, the propellant is a hydrofluoroalkane selected from selected from 1,1,1,2-tetrafluoroethane (HFC-134a) and 1,1,1,2,3,3,3-Heptafluoropropane (HFC-227), and combinations thereof.

In one embodiment, the propellant is 1,1,1,2-tetrafluoroethane (HFC-134a).

In some embodiments, the propellant may be a chlorofluorocarbon (CFC) selected from CFC 11, CFC 12, and CFC 114, and combinations thereof.

It has been surprisingly discovered that a specific range of the propellant is required to produce homogeneous (single phase) compositions that dispense easily from pressurized containers in the form of a spray. Less than about 49% by weight of a propellant can be insufficient to ensure composition delivery, while greater than about 61% by weight of a propellant can cause phase separation of the composition in the canister (see Example 2).

In some embodiments, the compositions of the disclosure comprise from about 49% w/w to about 61% w/w propellant. In some embodiments, the compositions of the disclosure comprise from about 49% w/w to about 61% w/w 1,1,1,2-tetrafluoroethane (HFA-134a).

In some embodiments, the compositions of the disclosure comprise from about 49% w/w to about 54% w/w propellant. In some embodiments, the compositions of the disclosure comprise from about 49% w/w to about 54% w/w 1,1,1,2-tetrafluoroethane (HFA-134a).

In one embodiment, the compositions of the disclosure comprise about 49.5% w/w propellant. In one embodiment, the compositions of the disclosure comprise about 53.5% w/w propellant.

Film Forming Agent

In some embodiments, the composition of the disclosure comprises at least one film forming agent in order to form a film on topical administration to the oral mucosa. Forming a film may be advantageous to prolong retention time of the compositions in the mouth to maximize absorption in the oral cavity. Typically, the majority of the propellant component evaporates almost immediately, thereby concentrating the remaining formulation. The term "film forming agent" encompasses any agent that will form a film substantially in the absence of the propellant, or upon evaporation of the propellant and/or portion of the solvent.

In some embodiments, the film forming agent may be a polymer approved for oral administration. In some embodiments, the film forming agent is a polymer selected from polyvinyl pyrolidone, polyvinyl alcohol, acrylic polymers, acrylic copolymers, methacrylate polymers, methacrylate copolymers, polyvinyl acetate, cellulose based polymers, cellulose based copolymers, and combinations thereof. Other suitable film forming agents are provided in, e.g., U.S. Pat. No. 8,349,297.

In one embodiment, the film forming agent is a methacrylate copolymer, or specifically, a cationic copolymer of dimethylaminoethyl methacrylate, butyl methacrylate, and methyl methacrylate (e.g., poly(butylmethacrylate-co-(2-dimethylaminoethyl)methacrylate-co-methyl methacrylate); or Eudragit E100).

In some embodiments, the compositions of the disclosure may comprise about 0.1% w/w to about 1% w/w film forming agent, or about 0.1% w/w, or about 0.2% w/w, or about 0.3% w/w; or about 0.4% w/w, or about 0.5% w/w, or about 0.6% w/w, or about 0.7% w/w; or about 0.8% w/w, or about 0.9% w/w, or about 1.0% w/w of a film forming agent.

In one embodiment, the compositions of the disclosure may comprise about 0.5% w/w of a film forming agent.

In some embodiments, the compositions of the disclosure may comprise about 0.1% w/w to about 1% w/w film forming agent, or about 0.1% w/w, or about 0.2% w/w, or about 0.3% w/w, or about 0.4% w/w, or about 0.5% w/w, or about 0.6% w/w, or about 0.7% w/w; or about 0.8% w/w, or about 0.9% w/w, or about 1.0% w/w methacrylate copolymer, e.g., Eudragit E100.

In one embodiment, the compositions of the disclosure may comprise about 0.5% w/w methacrylate copolymer, e.g., Eudragit E100.

In some embodiments, the composition of the disclosure is free of film forming agents.

Hydrophobic Solvent

In some embodiments, the composition comprises at least one hydrophobic solvent. The hydrophobic solvents used in the compositions of the disclosure encompass solvents which are immiscible or at least substantially immiscible with water.

In some embodiments, the hydrophobic solvent may be an oil-based solvent. The term "oil-based" encompasses any nonpolar chemical substance that is in liquid form at ambient temperature and atmospheric pressure and is both hydrophobic and lipophilic. The oil-based solvent may be of animal, plant or synthetic origin. In some embodiments, the oil-based solvent comprises a vegetable oil. Non-limiting examples of suitable vegetable oils include hydrogenated vegetable oil, sesame oil, castor oil, soybean oil, olive oil, cotton seed oil, and peanut oil, or a combination thereof.

In one embodiment, the compositions of the disclosure may comprise an oil-based solvent selected from sesame oil, soybean oil, hydrogenated vegetable oil, and combinations thereof.

In one embodiment, the oil-based solvent is sesame oil.

In some embodiments, the hydrophobic solvent may be an alkane solvent. The term "alkane solvent" encompasses any linear, branched, or cyclic saturated hydrocarbon that is in liquid form at ambient temperature and atmospheric pressure. An alkane solvent would thus typically be a lower alkane, e.g., a $C_5$ to $C_{12}$ alkane. In some embodiments, the alkane solvent may be selected from pentane, hexane, heptane, and combinations thereof.

In some embodiments, the hydrophobic solvent may be present in the composition of the disclosure at about 2% w/w to about 10% w/w, or about 2% w/w, or about 3% w/w; or about 4% w/w; or about 5% w/w; or about 6% w/w, or about 7% w/w, or about 8% w/w, or about 9% w/w, or about 10% w/w of the composition.

In one embodiment, the hydrophobic solvent may be present in the composition of the disclosure at about 2% w/w of the composition. In one embodiment, the hydrophobic solvent may be present in the composition of the disclosure at about 7% w/w of the composition.

In some embodiments, the oil-based solvent may be present in the composition of the disclosure at about 2% w/w to about 10% w/w, or about 2% w/w; or about 3% w/w, or about 4% w/w, or about 5% w/w, or about 6% w/w, or about 7% w/w, or about 8% w/w, or about 9% w/w, or about 10% w/w of the composition.

In one embodiment, the oil-based solvent may be present in the composition of the disclosure at about 2% w/w of the composition. In one embodiment, the oil-based solvent may be present in the composition of the disclosure at about 7% w/w of the composition.

In some embodiments, the alkane solvent may be present in the composition of the disclosure at about 2% w/w to about 10% w/w, or about 2% w/w, or about 3% w/w, or about 4% w/w, or about 5% w/w, or about 6% w/w, or about 7% w/w, or about 8% w/w, or about 9% w/w; or about 10% w/w of the composition.

In some embodiments, sesame oil may be present in the composition of the disclosure at about 2% w/w to about 10% w/w, or about 2% w/w, or about 3% w/w, or about 4% w/w; or about 5% w/w, or about 6% w/w, or about 7% w/w, or about 8% w/w, or about 9% w/w; or about 10% w/w of the composition.

In one embodiment, sesame oil may be present in the composition of the disclosure a about 2% w/w of the composition. In one embodiment, sesame oil may be present in the composition of the disclosure at about 2.2% w/w of the composition. In one embodiment, sesame oil may be present in the composition of the disclosure at about 2.17% w/w of the composition.

In one embodiment, sesame oil may be present in the composition of the disclosure at about 7% w/w of the composition. In one embodiment, sesame oil may be present in the composition of the disclosure at about 7.2% w/w of the composition.

In some embodiments, the composition of the disclosure is substantially anhydrous.

Alcohol-Based Solvent

The compositions of the present disclosure comprise at least one alcohol-based solvent as a carrier. An alcohol-based solvent, as used herein, is an organic solvent comprising an alcohol (—OH) group which is miscible, substantially miscible, or partially miscible with water. In some embodiments, lower alkyl (e.g., $C_1$-$C_{12}$) alcohols are used as alcohol-based solvents in the compositions of the disclosure. In some embodiments, suitable alcohol-based solvents are selected from ethanol, isopropanol, and n-propanol.

In one embodiment, the alcohol-based solvent is isopropyl alcohol, also known as isopropanol.

In some embodiments, the alcohol-based solvent may be present in the composition of the disclosure at about 30% w/w to about 60% w/w, or about 30% w/w to about 50% w/w, or about 30% w/w to about 45% w/w, or about 30% w/w, or about 35% w/w, or about 40% w/w; or about 45% w/w, or about 50% w/w of the composition.

In one embodiment, the alcohol-based solvent may be present in the compositions of the disclosure at about 40% w/w of the composition.

In some embodiments, isopropanol may be present in the composition of the disclosure at about 30% w/w to about 60% w/w, or about 30% w/w to about 50% w/w, or about 30% w/w to about 45% w/w, or about 30% w/w, or about 35% w/w, or about 40% w/w, or about 45% w/w, or about 50% w/w of the composition.

In one embodiment, the compositions of the disclosure comprise about 40% w/w isopropanol.

Co-Solvent

It has been surprisingly discovered that, in addition to a hydrophobic solvent and an alcohol-based solvent, incorporation of another solvent (that is, a co-solvent) into the cannabinoid formulations provides homogenous monophasic (single phase) formulations. As used herein, a "co-solvent" is a substance added to a composition comprising one or more primary solvents to increase solubility of the active agent and to impart other desirable properties to the composition. In some embodiments, the suitable co-solvent may be selected from benzyl alcohol (BA), propylene glycol (PG), dipropylene glycol (DiPG), glycerol, dimethicone 350, dimethicone 1000 and combinations thereof. In some embodiments, homogeneous compositions are provided comprising the co-solvent in an amount of about 0.5% w/w to about 5% w/w of the formulation.

In one embodiment, the co-solvent is benzyl alcohol.

In one embodiment, benzyl alcohol is incorporated into the formulations of the disclosure as a co-solvent. In some embodiments, the compositions of the disclosure may comprise 0.5% w/w to about 5% w/w, or about 1% w/w to about 3% w/w, or about 1.5% w/w to about 2% w/w, or about 2% w/w benzyl alcohol.

In another embodiment, the co-solvent is propylene glycol.

In one embodiment, propylene glycol is incorporated into the formulations of the disclosure as a co-solvent. In some embodiments, the compositions of the disclosure may comprise 0.5% w/w to about 5% w/w, or about 1% w/w to about 3% w/w, or about 1.5% w/w to about 2% w/w; or about 2% w/w propylene glycol.

In one embodiment, the pharmaceutical compositions of the disclosure further comprise a flavorant to impart a pleasant flavor to the formulation, which may aide in palatability. In some embodiments, the flavorant may be selected from, but are not limited to, menthol, levomenthol, peppermint flavoring, and cinnamon flavoring in a solvent, such as an alcohol-based solvent or an oil-based solvent.

Pharmaceutical Compositions Comprising a Film Forming Agent

In one aspect, the present disclosure provides pharmaceutical compositions comprising a cannabinoid, or a derivative thereof, a hydrophobic solvent, an alcohol-based solvent, an optional co-solvent, a film-forming agent, and about 49% w/w to about 61% w/w of a propellant, wherein the pharmaceutical composition is an oral liquid pharmaceutical composition, and wherein the pharmaceutical composition is substantially anhydrous.

In some embodiments, the pharmaceutical compositions of the disclosure are homogeneous. In one embodiment, the pharmaceutical compositions of the disclosure remain stable upon storage for at least two years at refrigerated temperature (e.g., about 2-8° C., or about 4° C.), or at least one month at room temperature (e.g., about 23° C.).

In one embodiment, the pharmaceutical composition of the disclosure is a single active pharmaceutical ingredient composition comprising a cannabinoid as the single pharmaceutical ingredient.

The pharmaceutical compositions of the disclosure comprise a cannabinoid, or a derivative thereof. In one embodiment, the cannabinoid is selected from (−)-trans-$\Delta^9$-tetrahydrocannabinol (dronabinol), cannabidiol (CBD), or pharmaceutically acceptable salts or derivatives thereof and combinations thereof. In one embodiment, the cannabinoid is (−)-trans-$\Delta^9$-tetrahydrocannabinol (dronabinol), or a pharmaceutically acceptable salt thereof. In one embodiment, the pharmaceutical compositions of the disclosure comprise from about 0.025% w/w to about 40% w/w of a cannabinoid. In one embodiment, the pharmaceutical compositions of the disclosure comprise from about 0.25% w/w to about 10% w/w of a cannabinoid. In one embodiment, the pharmaceutical compositions of the disclosure comprise from about 0.25% w/w to about 2% w/w of a cannabinoid.

In one embodiment, the pharmaceutical compositions comprise about 2% w/w to about 10% w/w of a hydrophobic solvent. In one embodiment, the pharmaceutical compositions comprise a hydrophobic solvent which is an oil-based solvent. In one embodiment, the hydrophobic solvent is an oil-based solvent selected from sesame oil, soy bean oil, hydrogenated vegetable oil, and combinations thereof. In one embodiment, the oil-based solvent is sesame oil.

In another embodiment, the pharmaceutical compositions comprise a hydrophobic solvent which is an alkane solvent, e.g., a $C_5$-$C_{12}$ alkane solvent. In one embodiment, the hydrophobic solvent is a $C_5$-$C_{12}$ alkane solvent selected from pentane, hexane, heptane, and combinations thereof.

In one embodiment, the pharmaceutical compositions comprise about 30% w/w to about 60% w/w of an alcohol-based solvent. In one embodiment, the pharmaceutical compositions comprise an alcohol-based solvent selected from ethanol, isopropanol, n-propanol and combinations thereof. In one embodiment, the alcohol-based solvent is isopropanol.

In one embodiment, the pharmaceutical compositions comprise about 0.5% w/w to about 5% w/w of a co-solvent. In one embodiment, the co-solvent is selected from benzyl alcohol, propylene glycol, dipropylene glycol, glycerol, dimethicone 350, dimethicone 1000 and combinations thereof. In one embodiment, the co-solvent is an additional alcohol-based solvent. In one embodiment, the co-solvent is benzyl alcohol. In one embodiment, the co-solvent is propylene glycol.

In one embodiment, the pharmaceutical compositions comprise about 0.1% w/w to about 1% w/w film forming agent. In one embodiment, the film forming agent is a polymer selected from polyvinyl pyrolidone, polyvinyl alcohol, acrylic polymers, acrylic copolymers, methacrylate polymers, methacrylate copolymers, polyvinyl acetate, cellulose based polymers, and cellulose based copolymers.

In one embodiment, the pharmaceutical compositions of the disclosure comprise from about 49% w/w to about 61% w/w of a propellant. In one embodiment, the pharmaceutical compositions of the disclosure comprise from about 49% w/w to about 54% w/w of a propellant. In one embodiment, the propellant is hydrofluoroalkane selected from 1,1,1,2-tetrafluoroethane (HFC-134a) and 1,1,1,2,3,3,3-Heptafluoropropane (HFC-227), or a chlorofluorocarbon selected from CFC 11, CFC 12, and CFC 114, and combinations thereof.

In one embodiment, the pharmaceutical composition according to the disclosure is substantially anhydrous and comprises:
  a. about 0.25% w/w to about 2% w/w of dronabinol, or a pharmaceutically acceptable salt thereof;
  b. about 2% w/w to about 10% w/w of a hydrophobic solvent (e.g., sesame oil);
  c. about 30% w/w to about 60% w/w of an alcohol-based solvent (e.g., isopropyl alcohol);
  d. about 0.5% w/w to about 5% w/w of a co-solvent (e.g., a co-solvent selected from benzyl alcohol and propylene glycol);
  e. about 0.1% w/w to about 1% w/w of a film forming agent (e.g., a cationic copolymer of dimethylaminoethyl methacrylate, butyl methacrylate, and methyl methacrylate (e.g., Eudragit E100)),
f. and about 49% w/w to about 61% w/w of a propellant (e.g., 1,1,1,2-tetrafluoroethane).

In one embodiment, the pharmaceutical composition according to the disclosure is substantially anhydrous and comprises:
a. about 0.8% w/w to about 2% w/w of dronabinol, or a pharmaceutically acceptable salt thereof;
b. about 2% w/w to about 8% w/w of a hydrophobic solvent (e.g., sesame oil);
c. about 40% w/w of an alcohol-based solvent (e.g., isopropyl alcohol);
d. about 2% w/w of a co-solvent (e.g., a co-solvent selected from benzyl alcohol and propylene glycol);
e. about 0.5% w/w of a film forming agent (e.g., a cationic copolymer of dimethylaminoethyl methacrylate, butyl methacrylate, and methyl methacrylate (e.g., Eudragit E100)),
f. and about 49% w/w to about 54% w/w of a propellant (e.g., 1,1,1,2-tetrafluoroethane).

In one embodiment, the pharmaceutical composition according to the disclosure is substantially anhydrous and comprises:
a. about 0.8% w/w of dronabinol, or a pharmaceutically acceptable salt thereof;
b. about 7.2% w/w of a hydrophobic solvent (e.g., sesame oil);
c. about 40% w/w of an alcohol-based solvent (e.g., isopropyl alcohol);
d. about 2.0% w/w of a co-solvent (e.g., benzyl alcohol);
e. about 0.5% w/w of a film forming agent (e.g., a cationic copolymer of dimethylaminoethyl methacrylate, butyl methacrylate, and methyl methacrylate (e.g., Eudragit E100),
f. and about 49.5% w/w of a propellant (e.g., 1,1,1,2-tetrafluoroethane).

In another embodiment, the pharmaceutical composition according to the disclosure is substantially anhydrous and comprises:
a. about 2.0% w/w of dronabinol, or a pharmaceutically acceptable salt thereof;
b. about 2.2% w/w of a hydrophobic solvent (e.g., sesame oil);
c. about 40% w/w of an alcohol-based solvent (e.g., isopropyl alcohol);
d. about 2.0% w/w of a co-solvent (e.g., propylene glycol);
e. about 0.5% w/w of a film forming agent (e.g., a cationic copolymer of dimethylaminoethyl methacrylate, butyl methacrylate, and methyl methacrylate (e.g., Eudragit E100),
f. and about 53.3% w/w of a propellant (e.g., 1,1,1,2-tetrafluoroethane).

In one embodiment, the pharmaceutical compositions of the disclosure further comprise a flavorant.

Pharmaceutical Compositions Free from Film-Forming Agents

In one aspect, the present disclosure provides pharmaceutical compositions comprising a cannabinoid, or a derivative thereof, a hydrophobic solvent, an alcohol-based solvent, an optional co-solvent, and about 49% w/w to about 61% w/w of a propellant, wherein the pharmaceutical composition is an oral liquid pharmaceutical composition, and wherein the pharmaceutical composition is free from film-forming agents and substantially anhydrous.

In one embodiment, the pharmaceutical compositions of the disclosure are homogeneous. In one embodiment, the pharmaceutical compositions of the disclosure remain stable upon storage for at least two years at refrigerated temperature (e.g., about 2-8° C., or about 4° C.), or at least one month at room temperature (e.g., about 23° C.).

In one embodiment, the pharmaceutical composition of the disclosure is a single active pharmaceutical ingredient composition comprising a cannabinoid as the single pharmaceutical ingredient.

In one embodiment, the cannabinoid is selected from (−)-trans-$\Delta^9$-tetrahydrocannabinol (dronabinol), cannabidiol (CBD), or pharmaceutically acceptable salts or derivatives thereof and combinations thereof. In one embodiment, the cannabinoid is (−)-trans-$\Delta^9$-tetrahydrocannabinol (dronabinol), or a pharmaceutically acceptable salt thereof. In one embodiment, the pharmaceutical compositions of the disclosure comprise from about 0.025% w/w to about 40% w/w of a cannabinoid. In one embodiment, the pharmaceutical compositions of the disclosure comprise from about 0.25% w/w to about 10% w/w of a cannabinoid. In one embodiment, the pharmaceutical compositions of the disclosure comprise from about 0.25% w/w to about 2% w/w of a cannabinoid.

In one embodiment, the pharmaceutical compositions comprise about 2% w/w to about 10% w/w of a hydrophobic solvent. In one embodiment, the pharmaceutical compositions comprise a hydrophobic solvent which is an oil-based solvent. In one embodiment, the hydrophobic solvent is an oil-based solvent selected from sesame oil, soy bean oil, hydrogenated vegetable oil, and combinations thereof. In one embodiment, the oil-based solvent is sesame oil.

In another embodiment, the pharmaceutical compositions comprise a hydrophobic solvent which is an alkane solvent, e.g., a $C_5$-$C_{12}$ alkane solvent. In one embodiment, the hydrophobic solvent is a $C_5$-$C_{12}$ alkane solvent selected from pentane, hexane, heptane, and combinations thereof.

In one embodiment, the pharmaceutical compositions comprise about 30% w/w to about 60% w/w of an alcohol-based solvent. In one embodiment, the pharmaceutical compositions comprise an alcohol-based solvent selected from ethanol, isopropanol, n-propanol and combinations thereof. In one embodiment, the alcohol-based solvent is isopropanol.

In one embodiment, the pharmaceutical compositions comprise about 0.5% w/w to about 5% w/w of a co-solvent. In one embodiment, the co-solvent is selected from benzyl alcohol, propylene glycol, dipropylene glycol, glycerol, dimethicone 350, dimethicone 1000 and combinations thereof. In one embodiment, the co-solvent is an additional alcohol-based solvent. In one embodiment, the co-solvent is benzyl alcohol. In one embodiment, the co-solvent is propylene glycol.

In one embodiment, the pharmaceutical compositions of the disclosure comprise from about 49% w/w to about 61% w/w of a propellant. In one embodiment, the pharmaceutical compositions of the disclosure comprise from about 49% w/w to about 54% w/w of a propellant. In one embodiment, the propellant is hydrofluoroalkane selected from 1,1,1,2-tetrafluoroethane (HFC-134a) and 1,1,1,2,3,3,3-Heptafluoropropane (HFC-227), or a chlorofluorocarbon selected from CFC 11, CFC 12, and CFC 114, and combinations thereof.

In one embodiment, pharmaceutical composition according to the disclosure is free from film forming agents and substantially anhydrous and comprises:

a. about 0.25% w/w to about 10% w/w of dronabinol or a pharmaceutically acceptable salt thereof;
b. about 2% w/w to about 10% w/w of a hydrophobic solvent (e.g., sesame oil);
c. about 30% w/w to about 60% w/w of an alcohol-based solvent (e.g., isopropyl alcohol);
d. about 0.5% w/w to about 5% w/w of a co-solvent (e.g., propylene glycol),
e. and about 49% w/w to about 61% w/w of a propellant (e.g., 1,1,1,2-tetrafluoroethane).

In one embodiment, the pharmaceutical composition according to the disclosure is free from film forming agents and substantially anhydrous and comprises:
a. about 2% w/w dronabinol, or a pharmaceutically acceptable salt thereof;
b. about 2.2% w/w of a hydrophobic solvent (e.g., sesame oil);
c. about 40% w/w of an alcohol-based solvent (e.g., isopropyl alcohol);
d. about 2% w/w of a co-solvent (e.g., propylene glycol);
e. and about 53.8% w/w of a propellant (e.g., 1,1,1,2-tetrafluoroethane).

In one embodiment, the pharmaceutical compositions of the disclosure further comprise a flavorant.

Sprays for Oral Application Comprising a Film Forming Agent

In another aspect, the present disclosure provides a spray for oral application comprising an oral liquid composition comprising about 0.025% w/w to about 40% w/w cannabinoid, or a derivative thereof, a hydrophobic solvent, an alcohol-based solvent, an optional co-solvent, a film former, and about 49% w/w to about 61% w/w of a propellant, wherein the composition is substantially anhydrous. In one embodiment, the spray is for buccal application. In one embodiment, the spray is for sublingual application.

In one embodiment, the sprays of the disclosure comprise compositions that are homogeneous. In one embodiment, the sprays of the disclosure remain stable upon storage for at least two years at refrigerated temperature (e.g., about 2-8° C., or about 4° C.), or at least one month at room temperature (e.g., about 23° C.).

In one embodiment, the cannabinoid is (–)-trans-Δ$^9$-tetrahydrocannabinol (dronabinol), or a pharmaceutically acceptable salt or solvate thereof. In one embodiment, the spray comprises from about 0.025% w/w to about 40% w/w of a cannabinoid. In one embodiment, the spray comprises from about 0.25% w/w to about 10% w/w of a cannabinoid. In one embodiment, the spray comprises from about 0.25% w/w to about 2% w/w of a cannabinoid.

In one embodiment, the spray comprises a hydrophobic solvent which is an oil-based solvent. In one embodiment, the hydrophobic solvent is an oil-based solvent selected from sesame oil, soybean oil, hydrogenated vegetable oil, and combinations thereof. In one embodiment, the oil-based solvent is sesame oil.

In another embodiment, the spray comprises a hydrophobic solvent which is an alkane solvent, e.g., a $C_5$-$C_{12}$ alkane solvent. In one embodiment, the hydrophobic solvent is a $C_5$-$C_{12}$ alkane solvent selected from pentane, hexane, heptane, and combinations thereof.

In one embodiment, the spray according to the disclosure is substantially anhydrous and comprises an oral liquid composition comprising:
a. about 0.25% w/w to about 2% w/w dronabinol, or a pharmaceutically acceptable salt thereof;
b. about 2% w/w to about 10% w/w of a hydrophobic solvent (e.g., sesame oil);
c. about 30% w/w to about 60% w/w of an alcohol-based solvent (e.g., isopropyl alcohol);
d. about 0.5% w/w to about 5% w/w of a co-solvent (e.g., a co-solvent selected from benzyl alcohol and propylene glycol);
e. about 0.1% w/w to about 1% w/w of a film-forming agent (e.g., a cationic copolymer of dimethylaminoethyl methacrylate, butyl methacrylate, and methyl methacrylate (e.g., Eudragit E100)),
f. and about 49% w/w to about 61% w/w of a propellant (e.g., 1,1,1,2-tetrafluoroethane).

In one embodiment, the spray according to the disclosure is a multi-dose spray delivering between 20 and 200 microliters of the composition per dose. In one embodiment, the spray is contained in a metal canister. In one embodiment, the metal canister comprises between about 10 ml and about 100 ml of the composition.

In one embodiment, the spray according to the disclosure is substantially anhydrous and comprises an oral liquid composition comprising:
a. about 0.8% w/w to about 2% w/w dronabinol, or a pharmaceutically acceptable salt thereof;
b. about 2% w/w to about 8% w/w of a hydrophobic solvent (e.g., sesame oil);
c. about 40% w/w of an alcohol-based solvent (e.g., isopropyl alcohol);
d. about 2% w/w of a co-solvent (e.g. a co-solvent selected from benzyl alcohol and propylene glycol);
e. about 0.5% w/w of a film-forming agent (e.g., a cationic copolymer of dimethylaminoethyl methacrylate, butyl methacrylate, and methyl methacrylate (e.g., Eudragit E100)),
f. and about 49% w/w to about 54% w/w of a propellant (e.g., 1,1,1,2-tetrafluoroethane).

In one embodiment, the spray according to the disclosure is substantially anhydrous and comprises an oral liquid composition comprising:
a. about 0.8% w/w dronabinol, or a pharmaceutically acceptable salt thereof;
b. about 7.2% w/w of a hydrophobic solvent (e.g., sesame oil);
c. about 40% w/w of an alcohol-based solvent (e.g., isopropyl alcohol);
d. about 2.0% w/w of a co-solvent (e.g. benzyl alcohol);
e. about 0.5% w/w of a film-forming agent (e.g., a cationic copolymer of dimethylaminoethyl methacrylate, butyl methacrylate, and methyl methacrylate (e.g., Eudragit E100)),
f. and about 49.5% w/w of a propellant (e.g., 1,1,1,2-tetrafluoroethane).

In another embodiment, the spray according to the disclosure is substantially anhydrous and comprises an oral liquid composition comprising:
a. about 2.0% w/w dronabinol, or a pharmaceutically acceptable salt thereof;
b. about 2.2% w/w of a hydrophobic solvent (e.g., sesame oil);
c. about 40% w/w of an alcohol-based solvent (e.g., isopropyl alcohol);
d. about 2.0% w/w of a co-solvent (e.g. propylene glycol);
e. about 0.5% w/w of a film-forming agent (e.g., a cationic copolymer of dimethylaminoethyl methacrylate, butyl methacrylate, and methyl methacrylate (e.g., Eudragit E100)),
f. and about 53.3% w/w of a propellant (e.g., 1,1,1,2-tetrafluoroethane).

In one embodiment, the sprays of the disclosure further comprise a flavorant.

Sprays for Oral Application Free From Film Forming Agents

In another aspect, the present disclosure provides a spray for oral application comprising an oral liquid composition comprising a cannabinoid, or a derivative thereof, a hydrophobic solvent, an alcohol-based solvent, an optional co-solvent, and about 49% w/w to about 61% w/w of a propellant, wherein the composition is free from film-forming agents and substantially anhydrous. In one embodiment, the spray is for buccal application. In one embodiment, the spray is for sublingual application.

In one embodiment, the sprays of the disclosure comprise compositions that are homogeneous. In one embodiment, the sprays of the disclosure remain stable upon storage for at least two years at refrigerated temperature (e.g., about 2-8° C., or about 4° C.), or at least one month at room temperature (e.g., about 23° C.).

In one embodiment, the cannabinoid is (−)-trans-$\Delta^9$-tetrahydrocannabinol (dronabinol), or a pharmaceutically acceptable salt thereof. In one embodiment, the spray comprises from about 0.025% w/w to about 40% w/w of a cannabinoid. In one embodiment, the spray comprises from about 0.25% w/w to about 10% w/w of a cannabinoid. In one embodiment, the spray comprises from about 0.25% w/w to about 2% w/w of a cannabinoid.

In one embodiment, the spray comprises a hydrophobic solvent which is an oil-based solvent. In one embodiment, the hydrophobic solvent is an oil-based solvent selected from sesame oil, soybean oil, hydrogenated vegetable oil, and combinations thereof. In one embodiment, the oil-based solvent is sesame oil.

In another embodiment, the spray comprises a hydrophobic solvent which is an alkane solvent, e.g., a $C_5$-$C_{12}$ alkane solvent. In one embodiment, the hydrophobic solvent is a $C_5$-$C_{12}$ alkane solvent selected from pentane, hexane, heptane, and combinations thereof.

In one embodiment, the spray according to the disclosure is free from film forming agents and substantially anhydrous and comprises an oral liquid composition comprising:
  a. about 0.25% w/w to about 10% w/w dronabinol, or a pharmaceutically acceptable salt thereof;
  b. about 2% w/w to about 10% w/w of a hydrophobic solvent (e.g., sesame oil);
  c. about 30% w/w to about 60% w/w of an alcohol-based solvent (e.g., isopropyl alcohol);
  d. about 0.5% w/w to about 5% w/w of a co-solvent (e.g., propylene glycol),
  e. and about 49% w/w to about 61% w/w of a propellant (e.g., 1,1,1,2-tetrafluoroethane).

In one embodiment, the spray according to the disclosure is a multi-dose spray delivering between 20 and 200 microliters (μL) of the composition per dose. In one embodiment, the spray is contained in a metal canister. In one embodiment, the metal canister comprises between about 10 ml and about 100 ml of the composition.

In one embodiment, the spray according to the disclosure is free from film forming agents and substantially anhydrous and comprises an oral liquid composition comprising:
  a. about 2% w/w of dronabinol, or a pharmaceutically acceptable salt thereof;
  b. about 2.2% w/w of a hydrophobic solvent (e.g., sesame oil);
  c. about 40% w/w of an alcohol-based solvent (e.g., isopropyl alcohol);
  d. about 2% w/w of a co-solvent (e.g., propylene glycol);
  e. and about 53.8% w/w of a propellant (e.g., 1,1,1,2-tetrafluoroethane).

Spray Canister, Valve and Actuator Packaging

In one aspect, the present disclosure provides a spray dosage form for oral application, e.g., buccal or sublingual application, comprising a pharmaceutical composition according to the disclosure. In one embodiment, the spray dosage form is contained in a pressurized system comprising a canister, a valve, and an actuator.

The development of a formulation in a pressurized system requires the formulation to be stable when in contact with the propellant (e.g., HFA 134a) and the canister, valve and actuator material and coating. Cannabinoids, e.g., dronabinol, may potentially be unstable to metal contact and therefore canisters, valves and actuators where metal contact is minimized are preferred.

In one embodiment, the vessels and canisters used in contact with the pharmaceutical composition according to the disclosure are metal. In one embodiment, the vessels and canisters are stainless steel or anodized aluminum. In another embodiment, the vessels and canisters are glass.

Suitable canisters may include, but are not limited to, e.g., 3M fluorinated ethylene propylene (FEP) coated canisters and Presspart stainless steel and/or anodized aluminum canisters, which may optionally be coated or treated.

Suitable valves may include, but are not limited to, e.g., 3M stainless steel crimp valves, with and without corrosion resistance treatment, Bespak BK357 metal crimp valves, Rexam 2D, pMDI, and/or Inhalia valves, and Lindal Kemp 20 aluminum gold/silver anodized metal valves.

Suitable actuators may include, but are not limited to, Lindal actuators, e.g., KNM3, NM19, NM19R, NM33, NM170, and NM171: Presspart actuators, e.g., NM2, NM17, NM170, NM19, NM19R, and NM33; and Rexam actuators, e.g., 9180, 8940, 4234, and AA994.

Methods of Use

In some embodiments, the compositions and dosage forms of the disclosure are useful for treating, ameliorating, or alleviating the symptoms of pain (e.g., migraine, neuropathic pain, trigeminal pain), dementia (e.g., Alzheimer's disease, mild cognitive impairment), a sleep disorder (e.g., sleep apnea, narcolepsy), a movement disorder (e.g., Tourette's syndrome, Parkinson's disease), a mental disorder (e.g., posttraumatic stress disorder), or multiple sclerosis (e.g., pain associated with multiple sclerosis, incontinence associated with multiple sclerosis).

In some particular embodiments, the compositions and dosage forms of the disclosure are useful for treating migraines.

It has been observed that cannabinoids, and THC in particular, have shown potential in treatment of Alzheimer's disease. Recent data strongly suggest that THC could be a potential therapeutic treatment option for Alzheimer's disease through multiple functions and pathways. See Cao C, Li Y, Liu H, Bai G, Mayl J, Lin X, Sutherland K, Nabar N, Cai J. The potential therapeutic effects of THC on Alzheimer's disease. *Journal of Alzheimer's disease: JAD.* 42 (3): 973-84, 2014. Some animal data show reversed disease progression by THC. In some particular embodiments, the pharmaceutical compositions of the disclosure are useful for treating or preventing Alzheimer's disease.

In some particular embodiments, the compositions and dosage forms according to the disclosure may be used for the treatment for symptomatic relief of spasticity (muscle stiffness/spasm) and/or neuropathic pain due to multiple sclerosis (MS). In certain embodiments, the compositions and dosage forms of the disclosure are useful for the analgesic treatment for cancer patients. In certain embodiments, the cancer patients are those still experiencing pain while on opioid therapy.

In some particular embodiments, the compositions and dosage forms according to the disclosure can be used to treat chemotherapy-induced emesis, nausea, and/or vomiting in patients with cancer, to treat HIV/AIDS-related anorexia, and/or as an appetite stimulant.

In another aspect, the present disclosure provides a method of treating, ameliorating, or alleviating the symptoms of a disease, disorder or condition in a subject in need of such treatment, the method comprising administering to the subject a therapeutically effective amount of the pharmaceutical composition or dosage form of the disclosure. The disease, disorder or condition includes pain (e.g., migraine, neuropathic pain, trigeminal pain), dementia (e.g., Alzheimer's disease, mild cognitive impairment), a sleep disorder (e.g., sleep apnea, narcolepsy), a movement disorder (e.g., Tourette's syndrome, Parkinson's disease), a mental disorder (posttraumatic stress disorder), and multiple sclerosis (e.g., pain associated with multiple sclerosis, incontinence associated with multiple sclerosis).

In one embodiment, the present disclosure provides a method of treating migraine in a subject in need of such treatment, the method comprising administering to the subject a therapeutically effective amount of the pharmaceutical composition or dosage form of the disclosure.

In one embodiment, the present disclosure provides a method of treating, ameliorating, or alleviating the symptoms of Alzheimer's disease in a subject in need of such treatment, the method comprising administering to the subject a therapeutically effective amount of the pharmaceutical composition or dosage form of the disclosure.

In one embodiment, the present disclosure provides a method of treating or preventing Alzheimer's disease in a subject in need of such treatment, the method comprising administering to the subject a therapeutically effective amount of the pharmaceutical composition or dosage form of the disclosure.

In some embodiments, the compositions and dosage forms are administered at least once a day. In other embodiments, the administering occurs more than once a day, e.g., 2 times, 3 times, 4 times, 5 times, 6 times, 7 times, 8 times, 9 times, or 10 times a day. In one embodiment, the administering is once a day. In one embodiment, the administering is 2 times a day.

In some embodiments, the compositions and dosage forms of the disclosure are administered orally.

EXAMPLES

The following examples illustrate specific aspects of the instant description. The examples should not be construed as limiting, as the examples merely provide specific understanding and practice of the embodiments and their various aspects.

Permeation and Penetration Protocol

The release of dronabinol from the selected formulations was compared using a previously validated method based on the principles of the FDA's SUPAC-SS guidelines [FDA (CDER), 1997, Guidance for industry-SUPAC-SS Non-sterile Semisolid Dosage Form, Scale-up and post approval changes: Chemistry, manufacturing and controls: in vitro release testing and in vivo bioequivalence documentation], where 11 formulations, n=6 repetitions were investigated during the full scale study.

Figure 2:
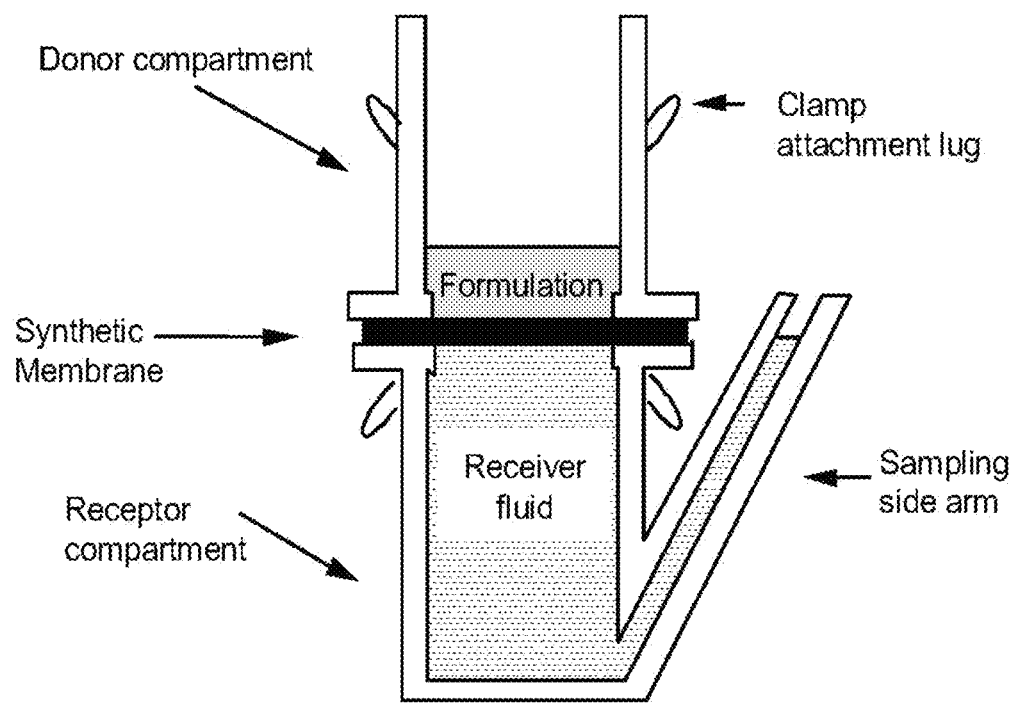
FIG. 2 depicts a schematic representation of a Franz cell.

The preliminary in vitro drug release study was performed using two formulations (H1, the 0.8% w/w formulation and one other 0.25% w/w formulation) in order to optimize the parameters to be employed during the full scale in vitro drug release experiment. The synthetic membranes employed during this study were selected based on a membrane binding study. The selected synthetic membranes were mounted between the donor and receptor compartment as shown in FIG. 2. Prior to performing the in vitro drug release study, the selected membranes were mounted between the donor and receptor compartment and the receptor chamber filled with receiver fluid in order to assess back diffusion though the synthetic membranes. Visual observations were made at t=24 and 48 h to assess if back diffusion of the receiver fluid into the donor compartment had occurred.

The parameters employed for the preliminary in vitro drug release experiment are as follows:
  (i) Individually calibrated Franz cells were employed where each cell had an average surface area and volume of approximately 2 $cm^2$ and 10 mL, respectively.
  (ii) Franz cells were mounted with selected membrane types, based on the binding experiments performed and filled with the receiver fluid (25% ethanol in water, 50% ethanol in water, or 2% Brij 98 w/v in 25% v/v ethanol in water).
  (iii) An additional Franz cell (n=1) was also mounted with the selected membrane but was not dosed with formulation to act as blanks.
  (iv) The Franz cells were equilibrated in a water bath pre-calibrated to 37° C. to achieve a membrane surface temperature of approximately 37° C.
  (v) An infinite dose (5 actuations, approx. 500 µL) of the selected formulation was applied to the surface of the Franz cells (n=2 for two active formulations (one 0.25% formulation and one 0.8% formulation), n=1 per placebo).
  (vi) Additional Franz cells were dosed with the 0.25% formulation (n=2, plus the placebo formulation at n=1), where the dosage was again an infinite dose (5 actuations) but each actuation was separated by one minute intervals.
  (vii) The Franz cells were protected from light for the duration of the investigation.
  (viii) At each time point 1 mL of the receiver fluid was removed from the Franz cell receptor compartment via the side-arm using a 1 mL syringe.
  (ix) After each 1 mL sample had been removed from the receptor compartment, 1 mL of fresh pre-heated receiver fluid was replaced, ensuring that no bubbles were present in the receptor compartment.
  (x) The time points for the initial experiment was: t=0, 1, 2, 4, 6, 24, 30 and 48 h, however, the Franz cells were maintained in the water bath and could have been sampled at additional time points until the samples were analyzed to confirm the in vitro drug release experiment had been completed, as evident by a plateau in the release of dronabinol.
  (xi) The samples were transferred into amber HPLC vials and analyzed using standard HPLC methodology.

Example 1: Preparation of Dronabinol Formulations

The formulations according to some embodiments of the present disclosure, were prepared as follows:
  (i) Premixes for the formulations were prepared in 10 g batches using the formulation weights detailed in Table 1. The premixes were prepared by the sequential weighing of the required quantities of dronabinol in sesame oil, isopropyl alcohol (IPA), co-solvent (benzyl alcohol, dipropylene glycol, and/or propylene glycol), flavorant (levomenthol, or peppermint flavor) and film forming agent (povidone, Eudragit E100, or Eudragit S100) into 20 mL borosilicate vials.

(ii) A PTFE magnetic follower was added to the formulation premix prepared from Step (i) and placed on magnetic stirrer plate to stir until the polymer was solvated and the formulation premix was observed to be miscible.

iii) The required amount of the specified premix (as detailed in Table 3) from Step (ii) was weighed into a 19 mL Presspart aluminium canister following the composition (g) in Table 3. The canisters were crimped with 20 mm 100 μL metered dose Lindal valves using the crimping device on the Pamasol aerosol filler (SOP 3088).

(iv) The canisters from Step (iii) were filled with the required quantity of HFA 134a (to prepare a 10 g batch) using the aerosol filling device of the Pamasol apparatus.

(v) The canisters were vigorously shaken by hand to ensure the premix and HFA 134a were mixed.

Tables 1 through 3, below, illustrate compositions according to various non-limiting embodiments of the disclosure.

TABLE 1

Compositions (% w/w) of active dronabinol formulations in canisters

| Excipients | H1 | L2 | L4 | L6 | L7 | L8 | L9 | O1 | O2 | O3 | O4 |
|---|---|---|---|---|---|---|---|---|---|---|---|
| Polymer (Povidone, E-100, S-100) | 0.50 | 0.50 | 0.50 | 0.50 | 0.50 | 0.50 | 0.50 | 0.50 | 0.50 | 0.50 | 0.50 |
| Dronabinol | 0.80 | 0.25 | 0.25 | 0.25 | 0.25 | 0.25 | 0.25 | 0.25 | 0.25 | 0.25 | 0.25 |
| Sesame Oil | 7.20 | 2.25 | 2.25 | 2.25 | 2.25 | 2.25 | 2.25 | 2.25 | 2.25 | 2.25 | 2.25 |
| IPA | 40.00 | 38.00 | 38.00 | 38.00 | 34.00 | 34.00 | 34.00 | 36.00 | 36.00 | 36.00 | 36.00 |
| Co-Solvents (PG/DiPG/BA) | 1.50 | — | 2.00 | 2.00 | 2.00 | 2.00 | 2.00 | 2.00 | 2.00 | 2.00 | 2.00 |
| L-Menthol/ Peppermint flavor | — | — | — | — | — | — | — | 0.10 | 0.015 | 0.05 | 0.01 |
| HFA 134a | 50.00 | 59.00 | 57.00 | 59.00 | 61.00 | 61.00 | 61.00 | 58.90 | 58.985 | 58.95 | 58.99 |
| Total | 100.00 | 100.00 | 100.00 | 100.00 | 100.00 | 100.00 | 100.00 | 100.00 | 100.00 | 100.00 | 100.00 |

— = not included

TABLE 2

Compositions (g) of active formulations as premixes to prepare a 10 g batch, prior to their preparation in the canister

| Excipients | H1 | L2 | L4 | L6 | L7 | L8 | L9 | O1 | O2 | O3 | O4 |
|---|---|---|---|---|---|---|---|---|---|---|---|
| Povidone | — | 0.122 ± 0.002 | 0.116 ± 0.002 | 0.122 ± 0.002 | — | 0.128 ± 0.003 | — | — | — | — | — |
| Eudragit E-100 | 0.100 ± 0.002 | — | — | — | 0.128 ± 0.003 | — | — | 0.122 ± 0.002 | 0.122 ± 0.002 | 0.122 ± 0.002 | 0.122 ± 0.002 |
| Eudragit S-100 | — | — | — | — | — | — | 0.128 ± 0.002 | — | — | — | — |
| Dronabinol in sesame oil | 1.800 ± 0.032 | 0.810 ± 0.012 | 0.581 ± 0.012 | 0.610 ± 0.012 | 0.641 ± 0.013 | 0.641 ± 0.013 | 0.641 ± 0.013 | 0.608 ± 0.012 | 0.809 ± 0.012 | 0.809 ± 0.012 | 0.810 ± 0.012 |
| IPA | 8.000 ± 0.16 | 9.268 ± 0.19 | 8.837 ± 0.18 | 5.781 ± 0.18 | 8.718 ± 0.17 | 8.718 ± 0.17 | 8.718 ± 0.17 | 8.759 ± 0.18 | 8.777 ± 0.18 | 8.770 ± 0.18 | 8.778 ± 0.18 |
| PG | — | — | 0.466 ± 0.009 | — | — | — | — | — | — | — | — |
| DiPG | — | — | — | 0.488 ± 0.010 | — | — | — | — | — | — | — |
| BA | 0.300 ± 0.006 | — | — | — | 0.513 ± 0.010 | 0.513 ± 0.010 | 0.513 ± 0.010 | 0.487 ± 0.010 | 0.485 ± 0.010 | 0.487 ± 0.010 | 0.488 ± 0.010 |
| L-Menthol | — | — | — | — | — | — | — | 0.024 ± 0.001 | 0.004 ± 0.0005 | — | — |
| Peppermint Flavour | — | — | — | — | — | — | — | — | — | 0.012 ± 0.001 | 0.002 ± 0.0005 |
| Total | 10.00 | 10.00 | 10.00 | 10.00 | 10.00 | 10.00 | 10.00 | 10.00 | 10.00 | 10.00 | 10.00 |

— = not included

TABLE 3

Compositions (g) of canister formulations, with the premix and HFA134a

| Formulation | Composition (g) Premix | HFA134a |
|---|---|---|
| H1 | 5.000 ± 0.1 | 5.000 ± 0.25 |
| L2 | 4.100 ± 0.08 | 5.900 ± 0.30 |
| L4 | 4.300 ± 0.09 | 5.700 ± 0.29 |
| L6 | 4.100 ± 0.08 | 5.900 ± 0.30 |
| L7 | 3.900 ± 0.08 | 6.100 ± 0.31 |
| L8 | 3.900 ± 0.08 | 6.100 ± 0.31 |
| L9 | 3.900 ± 0.08 | 6.100 ± 0.31 |
| O1 | 4.110 ± 0.08 | 5.890 ± 0.29 |
| O2 | 4.102 ± 0.08 | 5.899 ± 0.29 |
| O3 | 4.105 ± 0.08 | 5.895 ± 0.29 |
| O4 | 4.101 ± 0.08 | 5.899 ± 0.29 |

Example 2: Levels of Dronabinol (% w/w) in Canister

In some embodiments, formulations deliver between 0.25 mg and 2 mg dose of dronabinol after application. Table 4 details the % w/w dronabinol required in the canister to achieve such doses for different actuator volumes available (25, 50, 75, 85 and 100 ML). The miscibility of sesame oil in 40% IPA/HFA 134a has been determined to be 7.2% w/w, equivalent to 0.8% dronabinol, based on 10% w/v dronabinol in sesame oil. Therefore, the dose of dronabinol (mg) produced from each of the difference actuator volumes based on a level of 0.8% w/w dronabinol in canisters has been presented in Table 5.

TABLE 4

Calculated levels of dronabinol in canister (% w/w) required to achieve a dosage of 0.25 mg and 2.00 mg dronabinol with different actuator volumes

| Desired dose of dronabinol (mg) | Actuator Volume (μL) | Level of dronabinol in canister (% w/w) |
|---|---|---|
| 0.25 | 25 | 1.00 |
|  | 50 | 0.50 |
|  | 75 | 0.33 |
|  | 85 | 0.29 |
|  | 100 | 0.25 |
| 2.00 | 25 | 8.00 |
|  | 50 | 4.00 |
|  | 75 | 2.67 |
|  | 85 | 2.35 |
|  | 100 | 2.00 |

TABLE 5

Calculated dose of dronabinol for each actuator volume based on a level of 0.80% w/w dronabinol in canisters (max level observed from miscibility of sesame oil and HFA 134a experiments)

| Level of dronabinol in canister (% w/w) | Actuator Volume (μL) | Dose of dronabinol (mg) |
|---|---|---|
| 0.80 | 25 | 0.20 |
|  | 50 | 0.40 |
|  | 75 | 0.60 |
|  | 85 | 0.68 |
|  | 100 | 0.80 |

As Tables 4 and 5 demonstrate, using dronabinol in sesame oil, the desired dose of dronabinol (0.25-2.00 mg) is achievable with actuator volumes of 25-100 μL.

Example 3: Compositions with Varying Levels of HFA 134a

Compositions comprising dronabinol, isopropyl alcohol (IPA), sesame oil, benzyl alcohol as a co-solvent, a film forming agent (Eudragit E100, Eudragit S100, or Povidone), and HFA 134a as a propellant ranging in amounts from 57% w/w to 63% w/w were prepared and visually observed. The results are summarized in Table 6, below. Herein and throughout the Examples, the following abbreviations are used: SO (sesame oil), IPA (isopropyl alcohol), BA (benzyl alcohol), PG (propylene glycol), and DiPG (dipropylene glycol).

TABLE 6

Visual observations of formulations in canisters with higher levels of HFA 134a

| Formulation | Polymer | Dronabinol | Sesame oil (SO) | Isopropyl alcohol (IPA) | Benzyl alcohol (BA) | HFA 134a | Visual observations of premix | Visual observations in canister | Visual observations in canister after t = 24 h storage at 2-8° C. | Visual observations in canister after t = 72 h storage at 2-8° C. |
|---|---|---|---|---|---|---|---|---|---|---|
| F-IPA/SO/BA/ Eudragit E100-5 | 0.50 | 0.25 | 2.25 | 38.00 | 2.00 | 57.00 | Clear solution | Single phase | Single phase | Single phase |
| F-IPA/SO/BA/ Eudragit E100-6 | 0.50 | 0.25 | 2.25 | 36.00 | 2.00 | 59.00 | Clear solution | Single phase | Single phase | Single phase |
| F-IPA/SO/BA/ Eudragit E100-7 | 0.50 | 0.25 | 2.25 | 34.00 | 2.00 | 61.00 | Clear solution | Single phase | Single phase | Single phase |
| F-IPA/SO/BA/ Eudragit E100-7 | 0.50 | 0.25 | 2.25 | 32.00 | 2.00 | 63.00 | Clear solution | Single phase | 2-phases | 2-phases |
| F-IPA/SO/BA/ Povidone-8 | 0.50 | 0.25 | 2.25 | 38.00 | 2.00 | 57.00 | Clear solution | Single phase | Single phase | Single phase |
| F-IPA/SO/BA/ Povidone-9 | 0.50 | 0.25 | 2.25 | 36.00 | 2.00 | 59.00 | Clear solution | Single phase | Single phase | Single phase |

TABLE 6-continued

Visual observations of formulations in canisters with higher levels of HFA 134a

| Formulation | Composition (% w/w) | | | | | | Visual observations of premix | Visual observations in canister | Visual observations in canister after t = 24 h storage at 2-8° C. | Visual observations in canister after t = 72 h storage at 2-8° C. |
| --- | --- | --- | --- | --- | --- | --- | --- | --- | --- | --- |
| | Polymer | Dronabinol | Sesame oil (SO) | Isopropyl alcohol (IPA) | Benzyl alcohol (BA) | HFA 134a | | | | |
| F-IPA/SO/BA/ Povidone-10 | 0.50 | 0.25 | 2.25 | 34.00 | 2.00 | 61.00 | Clear solution | Single phase | Single phase | Single phase |
| F-IPA/SO/BA/ Povidone-11 | 0.50 | 0.25 | 2.25 | 32.00 | 2.00 | 63.00 | Clear solution | Single phase | 2-phases | 2-phases |
| F-IPA/SO/BA/ Eudragit S100-2 | 0.50 | 0.25 | 2.25 | 38.00 | 2.00 | 57.00 | Clear solution | Single phase | Single phase | Single phase |
| F-IPA/SO/BA/ Eudragit S100-3 | 0.50 | 0.25 | 2.25 | 36.00 | 2.00 | 59.00 | Clear solution | Single phase | Single phase | Single phase |
| F-IPA/SO/BA/ Eudragit S100-4 | 0.50 | 0.25 | 2.25 | 34.00 | 2.00 | 61.00 | Clear solution | Single phase | Single phase | Single phase |
| F-IPA/SO/BA/ Eudragit S100-5 | 0.50 | 0.25 | 2.25 | 32.00 | 2.00 | 63.00 | Clear solution | Single phase | 2-phases | 2-phases |

As the results in Table 6 indicate, compositions comprising up to 61% of a propellant (i.e., HFA 134a) were stable and remained homogeneous with no phase separation for at least 72 hours of storage at 2-8° C.

Example 4: Compositions Comprising a Flavorant

Flavorants, such as levomenthol and peppermint flavoring, were incorporated into dronabinol in sesame oil (2.25% w/w) formulations containing benzyl alcohol as the co-solvent. The composition (% w/w) and the visual observations of the formulations with high concentration of levomenthol (0.1% w/w) and peppermint flavoring (0.05% w/w) are summarized in Table 7, below.

As shown in Table 7, above, all formulations were observed to be a single phase and therefore physically compatible.

Example 5: Stability Investigations

Formulations with varying film forming agents (Eudragit E100 and povidone) and varying amounts of isopropanol, benzyl alcohol, and propellant were prepared and their stabilities investigated. A summary of the results is presented in Table 8, below.

TABLE 7

Visual observations of formulations with flavorants

| Formulation | Composition (% w/w) | | | | | | | Visual observations of premix | Visual observations of canister | Visual observations in canister after t = 72 h storage at 2-8° C. |
| --- | --- | --- | --- | --- | --- | --- | --- | --- | --- | --- |
| | Eudragit E100 | Dronabinol | Sesame oil | IPA | BA | Flavorant | HFA 134a | | | |
| OL1P (P-IPA/SO/BA/ L-Menthol/ Edragit E100-1) | 0.50 | 0.25 | 2.25 | 38.00 | 2.00 | 0.10 | 56.90 | Clear solution | Single phase | Single phase |
| OL1P (P-IPA/SO/BA/ L-Menthol/ Eudragit E100-2) | 0.50 | 0.25 | 2.25 | 36.00 | 2.00 | 0.10 | 58.90 | Clear solution | Single phase | Single phase |
| OL3P (P-IPA/SO/BA/ Peppermint flavor/Eudragit E100-1) | 0.50 | 0.25 | 2.25 | 38.00 | 2.00 | 0.05 | 56.95 | Clear solution | Single phase | Single phase |
| OL3P (P-IPA/SO/BA/ Peppermint flavor/Eudragit E100-1) | 0.50 | 0.25 | 2.25 | 36.00 | 2.00 | 0.05 | 58.95 | Clear solution | Single phase | Single phase |

TABLE 8

Visual observations of 0.8 mg dronabinol formulations in canisters

| Formulation | Composition (% w/w) | | | | | | Visual observations of premix | Visual observations of canister | Visual observations in canister after t = 24 h storage at 2-8° C. |
| --- | --- | --- | --- | --- | --- | --- | --- | --- | --- |
| | Film forming agent | Drona-binol | Sesame oil | IPA | BA | HFA 134a | | | |
| F-IPA/SO/BA/Eudragit E100-1 | 0.50 | 0.80 | 7.20 | 40.00 | 1.50 | 50.00 | Clear solution | Single phase | Single phase |
| F-IPA/SO/BA/Eudragit E100-2 | 0.50 | 0.80 | 7.20 | 37.50 | 1.50 | 52.50 | Clear solution | 2-phases | 2-phases |
| F-IPA/SO/BA/Eudragit E100-3 | 0.50 | 0.80 | 7.20 | 38.50 | 1.50 | 51.50 | Clear solution | 2-phases | 2-phases |
| F-IPA/SO/BA/Povidone-1 | 0.50 | 0.80 | 7.20 | 40.00 | 1.50 | 50.00 | Clear solution | Single phase | 2-phases |
| F-IPA/SO/BA/Povidone-2 | 0.50 | 0.80 | 7.20 | 37.50 | 1.50 | 52.50 | Clear solution | 2-phases | N/A |
| F-IPA/SO/BA/Povidone-3 | 0.50 | 0.80 | 7.20 | 38.00 | 1.50 | 52.00 | Clear solution | 2-phases | N/A |
| F-IPA/SO/BA/Povidone-4 | 0.50 | 0.80 | 7.20 | 39.00 | 1.50 | 51.00 | Clear solution | 2-phases | N/A |
| F-IPA/SO/BA/Povidone-5 | 0.50 | 0.80 | 7.20 | 40.00 | 2.00 | 49.50 | Clear solution | Single phase | 2-phases |
| F-IPA/SO/BA/Povidone-6 | 0.50 | 0.80 | 7.20 | 40.00 | 2.50 | 49.50 | Clear solution | Single phase | 2-phases |

Example 6: Stability Assessment of Dronabinol Formulations

The composition (% w/w) of each formulation selected and prepared for stability are summarized in Table 9 to incorporate the following:

The higher level of dronabinol in sesame oil (0.8% w/w)
The lower level of dronabinol in sesame oil (0.25% w/w)
Different polymers, i.e. Povidone, Eudragit E100 and S100
Different co-solvents, i.e. benzyl alcohol, propylene glycol and dipropylene glycol
Flavorants, i.e. levomenthol and peppermint flavoring Each formulation was prepared in both 19 mL Presspart stainless steel canisters and 10 mL glass canisters using 100 µL metered dose Lindal valves. For each formulation (active and placebo) 2 stainless steel canisters were prepared per time point (t=2 and 4 weeks) and condition (25 and 2-8° C.) and 1 glass canister per condition. Formulations were analyzed for dronabinol recovery, percentage peak purity and visual compatibility at each time point and condition.

TABLE 9

Compositions of active formulations in canisters, % w/w

| Formulation | Composition (% w/w) | | | | | | |
| --- | --- | --- | --- | --- | --- | --- | --- |
| | Eudragit E100 | Drona-binol | Sesame oil | IPA | Co-solvent (BA/PG/DiPG) | Flavorant | HFA 134a |
| H1 (F-IPA/SO/BA/Eudragit E100-1) | 0.50 | 0.80 | 7.20 | 40.00 | 1.50 | — | 50.00 |
| L1 (F-IPA/SO/Eudragit E100-2) | 0.50 | 0.25 | 2.25 | 38.00 | 0.00 | — | 59.00 |
| L2 (F-IPA/SO/Povidone-2) | 0.50 | 0.25 | 2.25 | 38.00 | 0.00 | — | 59.00 |
| L3 (F-IPA/SO/PG/Eudragit E100-2) | 0.50 | 0.25 | 2.25 | 38.00 | 2.00 | — | 57.00 |
| L4 (F-IPA/SO/PG Povidone-2) | 0.50 | 0.25 | 2.25 | 38.00 | 2.00 | — | 57.00 |
| L5 (F-IPA/SO/DiPG/Eudragit E100-3) | 0.50 | 0.25 | 2.25 | 36.00 | 2.00 | — | 59.00 |
| L6 (F-IPA/SO/DiPG/Povidone-3) | 0.50 | 0.25 | 2.25 | 36.00 | 2.00 | — | 59.00 |
| L7 (F-IPA/SO/BA/Eudragit E100-7) | 0.50 | 0.25 | 2.25 | 34.00 | 2.00 | — | 61.00 |
| L8 (F-IPA/SO/BA/Povidone-10) | 0.50 | 0.25 | 2.25 | 34.00 | 2.00 | — | 61.00 |
| L9 (F-IPA/SO/BA/Eudragit S100-4) | 0.50 | 0.25 | 2.25 | 34.00 | 2.00 | — | 61.00 |
| O1 (F-IPA/SO/BA/L-Menthol/Eudragit E100-9) | 0.50 | 0.25 | 2.25 | 36.00 | 2.00 | 0.1 | 58.90 |

TABLE 9-continued

Compositions of active formulations in canisters, % w/w

| Formulation | Composition (% w/w) | | | | | | |
|---|---|---|---|---|---|---|---|
| | Eudragit E100 | Drona-binol | Sesame oil | IPA | Co-solvent (BA/PG/DiPG) | Flavorant | HFA 134a |
| O2 (F-IPA/SO/BA/ L-Menthol/Eudragit E100-10) | 0.50 | 0.25 | 2.25 | 36.00 | 2.00 | 0.015 | 58.985 |
| O3 (F-IPA/SO/BA/ Peppermint oil/ Eudragit E100-9) | 0.50 | 0.25 | 2.25 | 36.00 | 2.00 | 0.05 | 58.95 |
| O4 (F-IPA/SO/BA/ Peppermint oil/ Eudragit E100-10) | 0.50 | 0.25 | 2.25 | 36.00 | 2.00 | 0.01 | 58.99 |

All formulations were observed to be a single phase after t=2 weeks storage at both 2-8° C. and 25° C. with the exception of Formulation H1, where phase separation was observed at 2-8° C. Since H1 was observed to be a single phase after t=2 weeks storage at 25° C. and only observed to phase separate at the lower temperature, this would suggest that only minor modifications to the levels of IPA and BA should be required to improve physical stability and achieve a single phase formulation. After t=4 weeks storage at 2-8° C. formulations L3, L4, L5 and L6 were also observed to have phase separated. Similar to formulation H1, modifications to the levels of IPA and BA can be performed to improve physical stability of the formulation.

Example 7: Full Scale In Vitro Permeation and Penetration of Dronabinol Formulations A full scale in vitro permeation and penetration study was conducted to assess the delivery of dronabinol across the buccal membrane from dronabinol formulations according to the disclosure (with and without film forming agent ("polymer")) in comparison with a commercial dronabinol spray product, Sativex®. These experiments were performed using porcine buccal membrane, which, unlike rat buccal membrane, is non-keratinised and comparable to human buccal membrane. No swallowing is involved in this model, where the inclusion of a film forming agent (polymer) is expected to increase the mucoadhesive properties of the film forming agent-containing formulations in vivo and further enhance dronabinol permeation compared to Sativex and other formulations without polymer. The following formulations were investigated. Formulation H1v2 comprises:
a. 0.8% w/w dronabinol;
b. 7.2% w/w sesame oil;
c. 40.0% w/w isopropyl alcohol;
d. 2.0% w/w benzyl alcohol;
e. 0.5% w/w Eudragit E100,
f. and 49.5% w/w 1,1,1,2-tetrafluoroethane.

Formulation H1C6 (also known as H1C6 with polymer because it comprises a film forming agent) comprises:
a. 2.0% w/w dronabinol;
b. 2.17% w/w sesame oil;
c. 40.0% w/w isopropyl alcohol;
d. 2.0% w/w propylene glycol;
e. 0.5% w/w Eudragit E100,
f. and 53.33% w/w 1,1,1,2-tetrafluoroethane.

Formulation H1V6NP, also known as H1C6 No Polymer, comprises:
a. 2.0% w/w dronabinol;
b. 2.17% w/w sesame oil;
c. 40.0% w/w isopropyl alcohol;
d. 2.0% w/w propylene glycol;
e. and 53.83% w/w 1,1,1,2-tetrafluoroethane.

Formulation L4v2 comprises:
a. 0.25% w/w dronabinol;
b. 2.25% w/w sesame oil;
c. 40.0% w/w isopropyl alcohol;
d. 2.0% w/w propylene glycol;
e. 0.5% w/w povidone,
f. and 55% w/w 1,1,1,2-tetrafluoroethane.

FIG. 1 shows the mean amount of dronabinol recovered (μg) following the final time point (t=24 h) from the donor chamber, surface, buccal membrane, receiver fluid and buccal+RF (combination of buccal membrane and receiver fluid) (n=6; ±SEM).

As shown in FIG. 1, it has been observed that the highest levels of dronabinol were recovered from the donor chamber and on the surface of the buccal membrane for all formulations tested.

The highest amount of dronabinol (μg) recovered from the buccal membrane was following the application of H1C6 with polymer in which 56.49±9.56 μg was recovered. The lowest recovery of dronabinol from the buccal membrane was L4v2 no polymer in which 6.67±0.57 μg was recovered. The rank order from highest to lowest amount of dronabinol recovered from the buccal membrane was as follows: H1C6 with polymer>H1C6 no polymer>Sativex>L4v2 with polymer>H1v2 with polymer>H1v2 no polymer>L4v2 no polymer. H1C6 with polymer showed statistically higher (p<0.05) amounts of dronabinol recovered from the buccal than L4v2 with polymer, H1v2 with polymer, H1v2 no polymer and L4v2 no polymer. Sativex only showed statistically higher (p<0.05) amounts of dronabinol recovered from the buccal membrane when compared to L4v2 no polymer.

It was observed that the level of dronabinol recovered from receiver fluid following 24 h was highest in samples dosed with H1C6 no polymer, in which 16.38±6.40 μg was recovered and the lowest recovery of dronabinol was observed in the H1v2 no polymer where 1.58±1.34 μg of dronabinol was observed. The rank order from highest to lowest amount of dronabinol recovered from receiver fluid following 24 h was as follows: H1C6 no polymer>Sativex>H1C6 with polymer>L4v2 with polymer>H1v2 with polymer>L4v2 no polymer>H1v2 no polymer. It can be noted that there was no statistical difference (p>0.05) across all formulations following the 24 h time point.

The effect of the polymer (Eudragit E100 or povidone) on the permeation of dronabinol into and through the buccal membrane can be seen for H1C6, L4v2 and H1v2 in which the amount of dronabinol recovered (μg) from the buccal membrane combined with receiver fluid (buccal+RF) decreased slightly with the removal of the polymer. For H1C6 with polymer (Eudragit E100) the combined total of dronabinol recovered from the buccal membrane and receiver fluid was observed to be 62.38±10.09 μg compared to H1C6 without Eudragit E100 where dronabinol recovery was observed to be 60.10±9.41 μg. For H1v2, the recovery of dronabinol from the buccal membrane and receiver fluid was observed to be 19.04±4.41 μg with polymer (Povidone) where lower amounts of dronabinol were observed with the same formulation without Povidone (13.35±3.41 μg). Following the application of L4v2 with polymer, the recovery of dronabinol from the buccal membrane and receiver fluid was observed to be 27.25±6.96 μg with polymer (Eudragit E100) and 9.29±1.39 μg without Eudragit E100. These results indicate that the presence of Eudragit E100 in the formulations did not appear to affect the permeation of dronabinol from the formulations.

As various changes can be made in the above-described subject matter without departing from the scope and spirit of the present disclosure, it is intended that all subject matter contained in the above description, or defined in the appended claims, be interpreted as descriptive and illustrative of the present disclosure. Many modifications and variations of the present disclosure are possible in light of the above teachings. Accordingly, the present description is intended to embrace all such alternatives, modifications, and variances which fall within the scope of the appended claims.

All patents, applications, publications, test methods, literature, and other materials cited herein are hereby incorporated by reference in their entirety as if physically present in this specification.

What is claimed is:

1. A spray comprising an oral liquid composition comprising about 0.025% w/w to about 40% w/w dronabinol or a pharmaceutical acceptable salt thereof, about 2% w/w to about 10% w/w of a hydrophobic solvent, about 30% w/w to about 60% w/w of an alcohol-based solvent, an optional co-solvent, about 0.5% of a film forming agent, and about 49% w/w to about 61% w/w of a propellant, wherein the composition is a single phase oral liquid composition which remains a single phase after two weeks of storage at 25° C. and is substantially anhydrous, and said spray is for oral application.

2. The spray of claim 1, wherein the spray is for buccal application or sublingual application.

3. The spray of claim 1, wherein the hydrophobic solvent is an oil-based solvent selected from the group of sesame oil, soybean oil, hydrogenated vegetable oil, and combinations thereof.

4. The spray of claim 1, wherein the hydrophobic solvent is a $C_5$-$C_{12}$ alkane solvent selected from the group of pentane, hexane, heptane, and combinations thereof.

5. The spray of claim 1, wherein the alcohol-based solvent is selected from the group of ethanol, isopropanol, n-propanol, and combinations thereof.

6. The spray of claim 1, wherein the co-solvent is present and selected from the group of benzyl alcohol, propylene glycol, dipropylene glycol, glycerol, dimethicone 350, dimethicone 1000, and combinations thereof.

7. The spray of claim 1, wherein the film forming agent is a polymer selected from the group of polyvinyl pyrolidone, polyvinyl alcohol, acrylic polymers, acrylic copolymers, methacrylate polymers, methacrylate copolymers, polyvinyl acetate, cellulose based polymers, cellulose based copolymers, and combinations thereof.

8. The spray of claim 1, wherein the film forming agent is a methacrylate copolymer.

9. The spray of claim 1, wherein the film forming agent is a cationic copolymer of dimethylaminoethyl methacrylate, butyl methacrylate, and methyl methacrylate.

10. The spray of claim 1, wherein the propellant is a hydrofluoroalkane selected from the group of 1,1,1,2-tetrafluoroethane (HFC-134a), 1,1,1,2,3,3,3-Heptafluoropropane (HFC-227), or a chlorofluorocarbon selected from CFC 11, CFC 12, and CFC 114, and combinations thereof.

11. A method of treating, ameliorating, or alleviating the symptoms of a disease, disorder or condition in a subject in need of such treatment, the method comprising administering to the subject a therapeutically effective amount of the spray of claim 1, wherein the disease, disorder or condition is selected from pain, dementia, a sleep disorder, a movement disorder, a mental disorder, and multiple sclerosis.

12. The method of claim 11, wherein the pain is migraine, neuropathic pain, or trigeminal pain.

13. The method of claim 11, wherein the dementia is Alzheimer's disease or mild cognitive impairment.

14. The method of claim 11, wherein the sleep disorder is sleep apnea or narcolepsy.

15. The method of claim 11, wherein the movement disorder is Tourette's syndrome or Parkinson's disease.

16. The method of claim 11, wherein the mental disorder is posttraumatic stress disorder.

17. The method of claim 11, wherein the pain is migraine.

18. The method of claim 11, wherein the dementia is Alzheimer's disease.

19. The method of claim 11, wherein the spray is administered at least once a day.

* * * * *